US008722858B2

(12) United States Patent
Yoshida

(10) Patent No.: US 8,722,858 B2
(45) Date of Patent: May 13, 2014

(54) ANTI-PROMININ-1 ANTIBODY HAVING ADCC ACTIVITY OR CDC ACTIVITY

(75) Inventor: Kenji Yoshida, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 552 days.

(21) Appl. No.: 12/666,418

(22) PCT Filed: Jun. 25, 2008

(86) PCT No.: PCT/JP2008/061516
§ 371 (c)(1), (2), (4) Date: Mar. 30, 2010

(87) PCT Pub. No.: WO2009/001840
PCT Pub. Date: Dec. 31, 2008

(65) Prior Publication Data
US 2010/0209439 A1 Aug. 19, 2010

(30) Foreign Application Priority Data
Jun. 25, 2007 (JP) ................................ 2007-166253

(51) Int. Cl.
*C12P 21/08* (2006.01)
*C07K 16/00* (2006.01)

(52) U.S. Cl.
USPC .................................... 530/387.3; 530/388.1

(58) Field of Classification Search
None
See application file for complete search history.

(56) References Cited

U.S. PATENT DOCUMENTS 5,843,633 A * 12/1998 Yin et al. ......................... 435/2
6,989,145 B2 * 1/2006 Shitara et al. ............. 424/144.1

FOREIGN PATENT DOCUMENTS

WO WO 2007/062138 A2 5/2007
WO WO 2008/070593 A2 6/2008

OTHER PUBLICATIONS

Fundamental Immunology, William E. Paul M.D., ed., 3rd Ed., pp. 292-295, 1993.*

Rudikoff et al. Proc. Natl. Acad. Sci. USA, 79(6):1979-1983, Mar. 1982.*

Colman P. M. Research in Immunology, 145:33-36, 1994.*

Bendig M. M., Methods: A Companion to Methods in Enzymology, 1995; 8:83-93.*

Portolano et Al. (Journal of Immunology, 1993, 150(3): 880-887).*

Little, M. et al., "Of mice and men: hybridoma and recombinant antibodies," *Immunol. Today 21*:364-370, Elsevier Science Ltd. (2000).

Presta, L. G., "Selection, design, and engineering of therapeutic antibodies," *J. Allergy Clin. Immunol. 116*:731-737, American Academy of Allergy, Asthma and Immunology (2005).

Smith, L.M. et al., "CD133/prominin-1 is a novel antibody therapeutic target in pancreatic, gastric and hepatocellular cancers," *Proceedings of the American Association for Cancer Research 48*:316, Abstract No. 1332 (2007).

Al-Hajj, M., et al., "Prospective identification of tumorigenic breast cancer cells," *Proc. Natl. Acad. Sci. U.S.A.* 100:3983-3988, National Academy of Science, United States (2003).

Bussolati, B., et al., "Isolation of Renal Progenitor Cells from Adult Human Kidney," *Am. J. Pathol.* 166:545-555, American Society for Investigative Pathology, United States (2005).

Collins, A.T., et al., "Prospective Identification of Tumorigenic Prostate Cancer Stem Cells," *Cancer Res.* 65:10946-10951, American Association for Cancer Research, United States (2005).

Dall'Acqua, W.F., et al., "Properties of Human IgG1s Engineered for Enhanced Binding to the Neonatal Fc Receptor (FcRn)," *J. Biol. Chem.* 281:23514-23524, The American Society for Biochemistry and Molecular Biology, Inc., United States (2006).

Ewert, S., et al., "Stability improvement of antibodies for extracellular and intracellular applications: CDR grafting to stable frameworks and structure-based framework engineering," *Methods* 34:184-199, Elsevier Inc., The Netherlands (2004).

Fargeas, C.A., et al., "AC133 Antigen, CD133, Prominin-1, Prominin-2, Etc.: Prominin Family Gene Products in Need of a Rational Nomenclature," *Stem Cells* 21:506-508, AlphaMed Press, Switzerland (2003).

Florek, M., et al., "Prominin-1/CD133, a neural and hematopoietic stem cell marker, is expressed in adult human differentiated cells and certain types of kidney cancer," *Cell Tissue Res.* 319:15-26, Springer-Verlag, Germany (2005).

Gehling, U.M., et al., "In vitro differentiation of endothelial cells from AC133—positive progenitor cells," *Blood* 95:3106-3112, American Society of Hematology, United States (2000).

Hodoniczky, J., et al., "Control of Recombinant Monoclonal Antibody Effector Functions by Fc *N*-Glycan Remodeling in Vitro," *Biotechnol. Prog.* 21:1644-1652, American Chemical Society and American Institute of Chemical Engineers, United States (2005).

Lazar, G.A., et al., "Engineered antibody Fc variants with enhanced effector function," *Proc. Natl. Acad. Sci. U.S.A.* 103:4005-4010, National Academy of Sciences, United States (2006).

(Continued)

*Primary Examiner* — Hong Sang
(74) *Attorney, Agent, or Firm* — Sterne, Kessler, Goldstein & Fox P.L.L.C.

(57) ABSTRACT

Disclosed are antibodies that bind to Prominin-1 and have ADCC activity and/or CDC activity, and pharmaceutical compositions containing those antibodies. Recombinant antibodies were produced by cloning a nucleotide sequence of the AC133 antibody variable region and it was discovered that the ADCC/CDC-inducing effect which does not exist in the original AC133 antibody is imparted to the recombinant antibodies. In the human chimeric antibody/human effector cell combination, the chimeric antibody whose constant region sequence had been converted to human IgG1/κ was found to induce strong ADCC. Humanized antibodies were prepared by grafting the AC133 antibody CDRs to a human antibody sequence, producing humanized antibodies having binding activities equivalent to the activity of the chimeric antibody. Also disclosed are unlabeled AC133 human chimeric antibodies and humanized antibodies having antitumor effects.

12 Claims, 11 Drawing Sheets

(56) References Cited

OTHER PUBLICATIONS

Matsumiya, S., et al., "Structural Comparison of Fucosylated and Nonfucosylated Fc Fragments of Human Immunoglobulin G1," *J. Mol. Biol.* 368:767-779, Elsevier Ltd., The Netherlands (2007).
Miraglia, S., et al., "A Novel Five-Transmembrane Hematopoietic Stem Cell Antigen: Isolation, Characterization, and Molecular Cloning," *Blood* 90:5013-5021, American Society of Hematology, United States (1997).
Niwa, R., et al., "Enhancement of the Antibody-Dependent Cellular Cytotoxicity of Low-Fucose IgG1 Is Independent of FcγRIIIa Functional Polymorphism," *Clin. Cancer Res.* 10:6248-6255, American Association for Cancer Research, United States (2004).
O'Brien, C.A., et al., "A human colon cancer cell capable of initiating tumour growth in immunodeficient mice," *Nature* 445:106-110, Nature Publishing Group, United Kingdom (2007).
Oganesyan, V., et al., "Structural characterization of a mutuated, ADCC-enhanced human Fc fragment," *Mol. Immunol.* 45:1872-1882, Elsevier Ltd., The Netherlands (2008).
Okazaki, A., et al., "Fucose Depletion from Human IgG1 Oligosaccharide Enhances Binding Enthalpy and Association Rate Between IgG1 and FcγRIIIa," *J. Mol. Biol.* 336:1239-1249, Elsevier Ltd., The Netherlands (2004).
Ono, K., et al., "The humanized anti-HM1.24 antibody effectively kills multiple myeloma cells by human effector cell-mediated cytotoxicity," *Mol. Immunol.* 36:387-395, Elsevier Science Ltd., The Netherlands (1999).
Pötgens, A.J.G., et al., "Human Trophoblast Contains an Intracellular Protein Reactive with an Antibody against CD133—A Novel Marker for Trophoblast," *Placenta* 22:639-645, Harcourt Publishers, United Kingdom (2001).
Pötgens, A.J.G., et al., "Monoclonal Antibody CD133-2 (AC141) Against Hematopoietic Stem Cell Antigen CD133 Shows Crossreactivity with Cytokeratin 18," *J. Histochem. Cytochem.* 50:1131-1134, The Histochemical Society, Inc., United States (2002).
Ricci-Vitiani, L., et al., "Identification and expansion of human colon-cancer-initiating cells," *Nature* 445:111-115, Nature Publishing Group, United Kingdom (2007).
Richardson, G.D., et al., "CD133, a novel marker for human prostatic epithelial stem cells," *J. Cell Sci.* 117:3539-3945, Company of Biologists, United Kingdom (2004).
Roguska, M.A., et al., "A comparison of two murine monoclonal antibodies humanized by CDR-grafting and variable domain resurfacing," *Protein Engineering* 9:895-904, Oxford University Press, United Kingdom (1996).
Shimozato, O., et al., "Antibody against cancer stem cell marker CD133 down-regulates cell cycle progression in colon cancer cells," The 66th Meeting of the Japanese Cancer Association, Nihon Gan Gakkai Gakujutsu Sokai Kiji, Dai 66 Kai, Aug. 2007, p. 51.
Shmelkov, S.V., et al., "AC133/CD133/Prominin-1," *Int. J. Biochem. Cel. Biol.* 37:715-719, Elsevier Ltd., The Netherlands (2005).
Singh, S.K., et al., "Identification of human brain tumour initiating cells," *Nature* 432:396-401, Nature Publishing Group, United Kingdom (2004).
Smith, L.M., et aL,"CD133/Prominin-1 Is a Novel Antibody Therapeutic Target in Pancreatic, Gastric and Hepatocellular Cancers," *Cancer Initiating Cell Therapeutic Potential:Poster Presentations*: Abstract #1332, 98th AACR Annual Meeting, Los Angeles, California, United States, Apr. 14-18, 2007.
Smith, L.M., et al.,"CD133/prominin-1 is a potential therapeutic target for antibody-drug conjugates in hepatoecellular and gastric cancers," *Br. J. Cancer* 99:100-109, Cancer Research, United Kingdom (2008).
Taylor, M.D., et al., "Radial glia cells are candidate stem cells of ependymoma," *Cancer Cell* 8:323-335, Elsevier Inc., The Netherlands (2005).
Thill, M., et al., "Identification of a population of $CD133^+$ precursor cells in the stroma of human cornea," *Invest. Ophthalmol. Vis. Sci.* 45: E-Abstract 3519, The Association for Research in Vision and Ophthalmology, United States (2004).
Van Orden, K., et al., "Proteomic analysis of colorectal tumor cells identifies CD133/Prominin-1, a cancer stem cell marker, as a monoclonal antibody therapeutic candidate," *Cancer Initiating Cell Therapeutic Potential:Poster Presentations*: Abstract #1324, 98th AACR Annual Meeting, Los Angeles, California, United States, Apr. 14-18, 2007.
Wu, H., et al., "Humanization of a Murine Monoclonal Antibody by Simultaneous Optimization of Framework and CDR Residues," *J. Mol. Biol.* 294:151-162, Academic Press, United Kingdom (1999).
Yin, A.H., et al., "AC133, a Novel Marker for Human Hematopoietic Stem and Progenitor Cells," *Blood* 90:5002-5012, American Society of Hematology, United States (1997).
International Search Report for International Application No. PCT/JP2008/061516, mailed on Aug. 19, 2008, Japanese Patent Office, Japan.
Carter, P.J., "Potent antibody therapeutics by design," *Nat. Rev. Immunol.* 6:343-357, Nature Publishing Group (2006).
Kusano, A. et al., "Immunocytochemical Study on Internalization of Anti-Carbohydrate Monoclonal Antibodies," *Anticancer Res.* 13:2207-2212, International Institute of Anticancer Research (1993).
Nimmerjahn, F. and Ravetch, J.V., "Divergent Immunoglobulin G Subclass Activity Through Selective Fc Receptor Binding," *Science* 310:1510-1512, American Association for the Advancement of Science (2005).
Peipp, M. et al., "Molecular Engineering III: Fc Engineering," *Handbook of Therpeutic Antibodies*, Dübel, S., ed., Ch. 8, pp. 171-196, Wiley-VCH Verlag GmbH & Co. KGaA (2007).
Bosslet, K., et al., "Immunological Tailoring of Monoclonal Antibodies for Immunotherapy of Pancreatic Carcinoma," *Int. J. Cancer: Supplement 2*:85-88, Alan R. Liss, Inc. (1988).
Huang, J. et al., "IgG Isotype Conversion of a Novel Human Anti-carcinoembryonic Antigen Antibody to Increase its Biological Activity," *Anticancer Research* 26:1057-1064, International Institute of Anticancer Research, Attiki, Greece (2006).
Scholz, D. et al., "Biological activity in the human system of isotype variants of oligosaccharide-Y-specific murine monoclonal antibodies," *Cancer Immunol. Immunother.* 33:153-157, Springer-Verlag (1991).

* cited by examiner (A)

```
AC133VH : 1   QVQLQQSGAELVRPGASVKLSCKASGYTFSXXXXXWVKQTPVHGLEWIGXXXXXXXXXXX 60
              QVQL QSGAE+ +PGASVK+SCKASGYTF+     WV+Q P  GLEW+G
AF174028: 58  QVQLVQSGAEVKKPGASVKVSCKASGYTFTSYGISWVRQAPGQGLEWMGWISAYNGNTNY 237

AC133VH : 61  XXXXXXKATLTTDKSSSTAYMELRSLTSEDSAVYYCTL-----------XXXXXWGQGTL 109
                    + T+TTD S+STAYMELRSL S+D+AVYYC L                WGQGTL
AF174028: 238 AQKLQGRVTMTTDTSTSTAYMELRSLRSDDTAVYYCALGGYCSGGSCPNNWFDPWGQGTL 417

AC133VH : 110 VTVSA 114  (SEQ ID NO:10)
              VTVS+
AF174028: 418 VTVSS 432  (SEQ ID NO:53)
```

(B)

```
AC133VL : 1   DVVVTQTPLSLPVSFGDQVSISCXXXXXXXXXXXXXXXXWYLHKPGQSPQLLIYXXXXXX 60
              DVV+TQ+PLSLPV+ G+  SISC                WYL KPGQSPQLLIY
AB064105: 67  DVVMTQSPLSLPVTPGEPASISCRSSQSLLHSNGYNYLDWYLQKPGQSPQLLIYLGSNRA 246

AC133VL : 61  XGVPDRFSGSGSGTDFTLKISTIKPEDLGMYYCXXXXXXXXXFGGGTKLEIKR 113 (SEQ ID NO:18)
               GVPDRFSGSGSGTDFTLKIS ++ ED+G+YYC         FG GTKLEIKR
AB064105: 247 SGVPDRFSGSGSGTDFTLKISRVEAEDVGVYYCMQALQTPYTFGQGTKLEIKR 405 (SEQ ID NO:54)
```

| | FR1 | CDR1 | FR2 | CDR2 | FR3 | CDR3 | FR4 | SEQ ID NO (POSITION) |
|---|---|---|---|---|---|---|---|---|
| h133VH | QVQLVQSGAEVKKPGASVKVSCKASGYTFT | DFEMH | WVRQAPGQGLEWMG | DIDPGTGDTAYNLKFKG | RVTMTTDTSTSTAYMELRSLRSDDTAVYYCAL | GAFVY | WGQGTLVTVSS | 32 (1-114) |
| mouse133VH | ----Q-----LVR------L---------S | ----- | --K-T-VH----I- | ----------------- | KA-L---K-S----------T-E-S-----T- | ----- | ----------A | 10 (1-114) |

(B)

| | FR1 | CDR1 | FR2 | CDR2 | FR3 | CDR3 | FR4 | SEQ ID NO (POSITION) |
|---|---|---|---|---|---|---|---|---|
| h133VL | DVVMTQSPLSLPVTPGEPASISC | RSSQSLANSYGNTYLS | WYLQKPGQSPQLLIY | GISNRFS | GVPDRFSGSGSGTDFTLKISRVEAEDVGVYYC | LQGTHQPYT | FGQGTKLEIK | 34 (1-112) |
| mouse133VL | ---V--T------SF-DQV---- | ---------------- | --H------------ | ------- | --------------------TIKP--L-M--- | --------- | --G------- | 18 (1-112) |
| hybridVL1 | ---V--T------SF-DQV---- | ---------------- | --------------- | ------- | -------------------------------- | --------- | ---------- | 36 (1-112) |
| hybridVL2 | ----------------------- | ---------------- | --H------------ | ------- | --------------------TIKP--L-M--- | --------- | --G------- | 38 (1-112) |
| h133VLb | ---V------------------- | ---------------- | --------------- | ------- | -------------------------------- | --------- | ---------- | 40 (1-112) |
| h133VLc | --------------F-------- | ---------------- | --------------- | ------- | -------------------------------- | --------- | ---------- | 42 (1-112) |
| h133VLd | -----------------Q----- | ---------------- | --------------- | ------- | -------------------------------- | --------- | ---------- | 44 (1-112) |
| h133VLe | --------------F--Q----- | ---------------- | --------------- | ------- | -------------------------------- | --------- | ---------- | 46 (1-112) |
| h133VLf | ------------------V---- | ---------------- | --------------- | ------- | -------------------------------- | --------- | ---------- | 48 (1-112) |
| h133VLg | --------------F---V---- | ---------------- | --------------- | ------- | -------------------------------- | --------- | ---------- | 50 (1-112) |
| h133VLh | --------------F--QV---- | ---------------- | --------------- | ------- | -------------------------------- | --------- | ---------- | 52 (1-112) |

FIG. 8

ANTI-PROMININ-1 ANTIBODY HAVING ADCC ACTIVITY OR CDC ACTIVITY

TECHNICAL FIELD

The present invention relates to antibodies that bind to Prominin-1 and have ADCC activity and/or CDC activity, and pharmaceutical compositions comprising those antibodies as an active ingredient.

BACKGROUND ART

AC133 was isolated as an antibody that recognizes hematopoietic stem cell markers (Non-patent Document 1), and is a mouse monoclonal antibody that recognizes the glycosylated structure of the five-transmembrane protein Prominin-1 (CD133) (Non-patent Document 2). The epitope recognized by AC133 has been reported to be present in endothelial precursor cells, tissue-specific stem cells/precursor cells, or such in addition to CD34-positive hematopoietic stem cells derived from fetal liver, bone marrow, and peripheral blood (Non-patent Documents 3 to 6). Furthermore, over-expression of Prominin-1 has been reported in a wide variety of tumor types such as blood tumors (AML and CLL) and solid tumors (various types of cancers such as colon, stomach, pancreatic, liver, kidney, and prostate cancer) (Non-patent Document 7). There is no simple correlation between epitope detection by the AC133 antibody and the expression of Prominin-1 gene or protein; and that is because of the presence of cell-specific post-translational sugar modification (Non-patent Documents 2 and 8).

In relation to over-expression of Prominin-1 in cancer, recently there are a series of reports that an undifferentiated secondary cell population having the AC133 epitope exists in cancer tissues, and repeated proliferation and differentiation of cancer stem cells included in this population causes tumor formation and maintenance. So far, such cancer stem cells have been found to exist in brain tumors (Non-patent Document 9), ependymoma (Non-patent Document 10), prostate cancer (Non-patent Document 11), breast cancer (Non-patent Document 12), and colon cancer (Non-patent Documents 13 and 14). When a small number of cancer cells enriched from a cancer tissue using the AC133 epitope (CD133) positivity as the indicator is transplanted into immunodeficient mice, formation of tumors histomorphologically similar to the original cancer tissues took place at high frequency, but on the other hand, tumor formation did not take place in the AC133 epitope-negative group even though the number of cells transplanted was tens of times greater. This result indicates that tumor growth may be suppressed by selectively eliminating cancer stem cells, and it is worth the attention as a novel therapeutic method for targeting cancer. Many of the conventional chemotherapeutic agents have non-specific growth suppression and cytotoxicity as their mechanism of action, and side effects on normal tissues have been therapeutically problematic. By targeting the proliferating undifferentiated cancer cells, it may be possible to suppress cancer metastasis, promote shrinking of primary tumor foci, and reduce side effects on normal cells.

Using models of SCID mice into which Hep3B cells have been transplanted, Smith et al. showed that AC133 antibodies labeled with a potent cytotoxic substance monomethyl auristatin F (MMAF) have an effect of reducing tumor volume (Non-patent Document 7). Since MMAF is a compound that does not penetrate through the cell membrane, incorporation of MMAF-labeled antibodies into cells is expected to be a process of the mechanism of the pharmaceutical agent.

Twenty years or more have past since the concept of cancer therapy using toxin-labeled antibodies was postulated, but there are unresolved problems in clinical application such as serious toxicity exhibited by the dissociated pharmaceutical agent on normal tissues. On the other hand, if one supposes that AC133 is quickly taken into cells after antigen binding, the possibility that antibody-dependent cellular cytotoxicity (ADCC) activity and complement-dependent cytotoxicity (CDC) activity are induced as a result of antibody binding may be low.

Prior art literature relating to the present invention of this application is shown below.

Non-patent Document 1: Yin et al., Blood (1997) 90: 5002-12

Non-patent Document 2: Miraglia et al., Blood (1997) 90: 5013-21

Non-patent Document 3: Gehling et al., Blood (2000) 95: 3106-12

Non-patent Document 4: Thill et al., Invest. Opthalmol. Vis. Sci. (2004) 45: U160, 3519

Non-patent Document 5: Bussolati et al., Am. J. Path. (2005) 166: 545-55

Non-patent Document 6: Richardson et al., J. Cell Sci. (2004) 117: 3539-45

Non-patent Document 7: Smith et al., AACR 100$^{th}$ Annual Meeting (2007) poster session #1332

Non-patent Document 8: Florek et al., Cell Tissue Res. (2005) 319: 15-26

Non-patent Document 9: Sheila et al., Nature (2004) 432: 396-401

Non-patent Document 10: Taylor et al., Cancer cell (2005) δ: 323-35

Non-patent Document 11: Collins et al., Cancer Res. (2005) 65: 10946-10951

Non-patent Document 12: Al-Hajj et al., Proc. Natl. Acad. Sci. USA (2003) 100: 3983-8

Non-patent Document 13: O'Brien et al., Nature (2007) 445: 106-110

Non-patent Document 14: Ricci-Vitiani et al., Nature (2007) 445: 111-5

DISCLOSURE OF THE INVENTION

Problems to be Solved by the Invention

The present invention was achieved in view of the above circumstances. An objective of the present invention is to provide antibodies that bind to Prominin-1 and have ADCC activity and/or CDC activity, and pharmaceutical compositions comprising those antibodies as an active ingredient.

Means for Solving the Problems

To solve the above-mentioned problems, the present inventors produced recombinant antibodies by cloning a nucleotide sequence of the AC133 antibody variable region, and discovered that the ADCC/CDC-inducing effect which does not exist in the original AC133 antibody is imparted to the recombinant antibodies, thereby completing the present invention. The mouse AC133 IgG1-subtype antibody produced by hybridomas did not show any CDC or ADCC effect. With the consideration that CDC induction was hardly observed in mouse IgG1-subtype antibodies, the present inventors first produced a recombinant IgG2a antibody in which the mouse IgG1 constant region sequence was substituted with an IgG2a sequence. CDC induction occurred but ADCC induction did not take place with the recombinant IgG2a mouse antibody. The level of antigen present in WERI-Rb-1 cells used as the target was determined to be sufficient for ADCC induction; thus the recombinant antibody may have been unsuitable in view of action mechanism because the AC133 epitope site was unsuitable for ADCC induction or the epitope-bound antibody complex was quickly internalized. However, by examining further through conversion of the constant region sequence into human IgG1/κ, the present inventors discovered that strong ADCC is induced by the human chimeric antibody/human effector cell combination.

Furthermore, the present inventors aimed to produce a humanized antibody by grafting the AC133 antibody CDR into a human antibody sequence. Humanization was carried out using AF174028 (H chain) and AB064105 (L chain) as antibody sequences for CDR grafting. Compared to the human chimeric antibody, its binding affinity to the antigen was low. However, further studies were carried out by introducing amino acid substitutions into the humanized L chain sequence, and the present inventors discovered that when the amino acid at position 15 in the humanized L chain variable region FR1 is Phe, and the amino acid at position 18 of the humanized L chain variable region FR1 is Gln, it has a binding activity equivalent to that of the chimeric antibody.

Conversion of mouse antibodies to human IgG1/κ or humanized antibodies, which are a more preferable molecular form, is advantageous from the standpoint of lowering immunogenicity when the antibodies are administered to humans as a pharmaceutical composition. The present invention provides unlabeled AC133 human chimeric antibodies and humanized antibodies having antitumor effect.

More specifically, the present invention provides (1) to (16) below:

(1) an antibody which binds to Prominin-1 and has ADCC activity or CDC activity;

(2) the antibody of (1), which recognizes a same epitope as the epitope recognized by the AC133 antibody;

(3) the antibody of (1) or (2), which is a chimeric antibody or a humanized antibody;

(4) the antibody of any one of (1) to (3), comprising the amino acid sequence of SEQ ID NO: 12 as a heavy chain variable region CDR1, the amino acid sequence of SEQ ID NO: 14 as a heavy chain variable region CDR2, and the amino acid sequence of SEQ ID NO: 16 as a heavy chain variable region CDR3;

(5) the antibody of any one of (1) to (4), comprising the amino acid sequence of SEQ ID NO: 20 as a light chain variable region CDR1, the amino acid sequence of SEQ ID NO: 22 as a light chain variable region CDR2, and the amino acid sequence of SEQ ID NO: 24 as a light chain variable region CDR3;

(6) the antibody of (5), wherein the amino acid at position 15 in a light chain variable region FR1 which corresponds to position 15 in the amino acid sequence of SEQ ID NO: 34 is Phe;

(7) the antibody of (6), wherein the amino acid at position 18 in a light chain variable region FR1 which corresponds to position 18 in the amino acid sequence of SEQ ID NO: 34 is Gln;

(8) an antibody of any of (a) to (f) below:

(a) an antibody comprising a heavy chain variable region comprising the amino acid sequence of positions 1 to 114 of SEQ ID NO: 32;

(b) an antibody comprising a light chain variable region comprising the amino acid sequence of positions 1 to 112 of SEQ ID NO: 42;

(c) an antibody comprising a light chain variable region comprising the amino acid sequence of positions 1 to 112 of SEQ ID NO: 46;

(d) an antibody comprising a heavy chain variable region comprising the amino acid sequence of positions 1 to 114 of SEQ ID NO: 32 and a light chain variable region comprising the amino acid sequence of positions 1 to 112 of SEQ ID NO: 42;

(e) an antibody comprising a heavy chain variable region comprising the amino acid sequence of positions 1 to 114 of SEQ ID NO: 32 and a light chain variable region comprising the amino acid sequence of positions 1 to 112 of SEQ ID NO: 46; and (f) an antibody functionally equivalent to the antibody of any of (a) to (e);

(9) the antibody of any one of (1) to (8), wherein the heavy chain constant region is not mouse IgG1;

(10) the antibody of (9), wherein the heavy chain constant region is human IgG1 and the light chain constant region is human Igκ;

(11) the antibody of (10), not bound by a cytotoxic substance;

(12) a pharmaceutical composition comprising the antibody of any one of (1) to (11) as an active ingredient;

(13) the pharmaceutical composition of (12), which is an anticancer agent;

(14) a method for preventing or treating cancer, which comprises the step of administering the antibody of any one of (1) to (11) to a subject;

(15) use of the antibody of any one of (1) to (11) in producing an anticancer agent; and

(16) the antibody of any one of (1) to (11), which is used for a method for treating cancer.

BRIEF DESCRIPTION OF THE DRAWINGS

FIG. 5 shows alignment of the human antibody variable region sequences and AC133 variable region sequences which serve as the target of CDR grafting. (A) shows the H chain variable region sequences and (B) shows the L chain variable region sequences.

FIG. 8 shows differences in the amino acid residues between the mouse sequence and humanized sequence, and amino acid residues that were substituted in the humanized sequence for improving the binding activity. (A) shows the H chain variable region sequence, and (B) shows the L chain variable region sequence.

MODE FOR CARRYING OUT THE INVENTION

Figure 1:
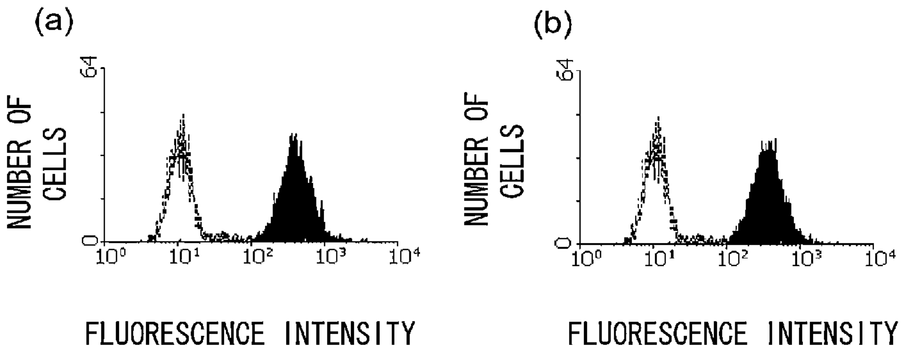
FIG. 1 shows binding of the recombinant antibodies to WERI-Rb-1 cells. The dotted-line histograms show the staining results obtained with the negative control mouse IgG antibody (5 μg/mL). The black-filled histograms show the staining results obtained with (a) the recombinant IgG2a antibody (5 μg/mL), and (b) the positive control hybridoma-produced IgG1 antibody (5 μg/mL).

The present invention relates to antibodies that bind to Prominin-1 and have ADCC activity and/or CDC activity, and pharmaceutical compositions comprising those antibodies as an active ingredient.

The present inventors produced recombinant antibodies by cloning a nucleotide sequence of the AC133 antibody variable region, and discovered that the ADCC/CDC-inducing effect which does not exist in the original AC133 antibody is imparted to the recombinant antibodies. The present invention is based on this finding.

The anti-Prominin-1 antibodies of the present invention may be of any origin (mouse, rat, human, or such), type (monoclonal antibody or polyclonal antibody), or form (altered antibodies, minibodies (low molecular weight antibodies), modified antibodies, etc.), and such, as long as they bind to Prominin-1.

In the present invention, Prominin-1 preferably means human Prominin-1. The nucleotide sequence and amino acid sequence of human Prominin-1 are already known (Miraglia et al., Blood (1997) 90: 5013-21; GenBank accession no. is NM_006017).

Preferably, anti-Prominin-1 antibodies of the present invention bind specifically to Prominin-1. Furthermore, anti-Prominin-1 antibodies of the present invention are preferably monoclonal antibodies.

These anti-Prominin-1 antibodies can be obtained by a method to be described later.

Anti-Prominin-1 antibodies of the present invention usually have antibody-dependent cellular cytotoxicity (ADCC) activity or complement-dependent cytotoxicity (CDC) activity, and preferably have both ADCC activity and CDC activity. In the present invention, CDC activity means cytotoxic activity mediated by a complement system. On the other hand, ADCC activity means an activity to cause injury in a target cell when a specific antibody attaches to a cell surface antigen of the target cell, and then an Fcγ receptor-containing cell (such as immunocyte) binds to the Fc moiety of the antibody via the Fcγ receptor.

Without particular limitation, antibodies of the present invention preferably have ADCC activity and/or CDC activity against cancer stem cells and cancer cells such as the human retinoblastoma cell line WERI-Rb-1.

ADCC activity or CDC activity can be measured by methods known to those skilled in the art (for example, Current protocols in Immunology, Chapter 7. Immunologic studies in humans, Editor, John E, Coligan et al., John Wiley & Sons, Inc., (1993), etc.)

Specifically, measurements can be taken, for example, by the following method.

First, effector cells, complement solution, and target cells are prepared.

(1) Preparation of Effector Cells

Spleen is removed from a CBA/N mouse or the like, and spleen cells are isolated in RPMI1640 medium (manufactured by Invitrogen). After washing with the same medium containing 10% fetal bovine serum (FBS, manufactured by HyClone), effector cells with a cell concentration adjusted to $5\times10^6$ cells/mL were prepared.

(2) Preparation of Complement Solution

Baby Rabbit Complement (manufactured by CEDARLANE) is diluted 10-fold with a culture medium (manufactured by Invitrogen) containing 10% FBS to prepare a complement solution.

(3) Preparation of Target Cells

Target cells can be radioactively labeled by incubating cells expressing the Prominin-1 protein with 0.2 mCi of sodium chromate-$^{51}$Cr (manufactured by GE Healthcare Bio-Sciences) in a DMEM medium containing 10% FBS for one hour at 37° C. For Prominin-1 protein-expressing cells, one may use cells transformed with a gene encoding the Prominin-1 protein, cancer cells (cancer stem cells, human retinoblastoma cell line WERI-Rb-1, etc.) or such. After radioactive labeling, cells are washed three times with RPMI1640 medium containing 10% FBS, and the target cells can be prepared by adjusting the cell concentration to $2\times10^5$ cells/mL.

ADCC activity and CDC activity can be measured by the method described below. In the case of ADCC activity measurement, 50 μL of the target cells and 50 μL of the anti-Prominin-1 antibody are each added to a 96-well U-bottom plate (manufactured by Becton Dickinson), and reacted for 15 minutes on ice. Thereafter, 100 μL of effector cells are added and incubated in a carbon dioxide incubator for four hours. The final concentration of the antibody is adjusted to 0 or 10 μg/mL. After incubation, 100 μL of the supernatant is collected, and radioactivity is measured with a gamma counter (COBRAII AUTO-GAMMA, MODEL D5005, manufactured by Packard Instrument Company). The cytotoxic activity (%) can be calculated using values obtained from the equation $(A-C)/(B-C)\times100$. A represents the radioactivity (cpm) in each sample, B represents the radioactivity (cpm) in a sample where 1% NP-40 (manufactured by Nacalai Tesque) has been added, and C represents the radioactivity (cpm) of a sample containing the target cells alone.

Meanwhile, in the case of CDC activity measurement, 50 μL of the target cells and 50 μL of the anti-Prominin-1 antibody are each added to a 96-well flat-bottom plate (manufactured by Becton Dickinson), and reacted for 15 minutes on ice. Thereafter, 100 μL of the complement solution is added, and incubated in a carbon dioxide incubator for four hours. The final concentration of the antibody is adjusted to 0 or 3 μg/mL. After incubation, 100 μL of the supernatant is collected, and radioactivity is measured with a gamma counter. The cytotoxic activity can be calculated by the same way as in the ADCC activity determination.

An example of a preferred embodiment of the antibodies of the present invention includes antibodies that recognize the same epitope as the AC133 antibody. AC133 is a known antibody, and it can be obtained from the hybridoma cell line HB-12346 deposited with ATCC.

It can be confirmed that a test antibody shares the epitope of a certain antibody when the two antibodies compete for the same epitope. Competition between antibodies can be detected by cross-blocking assay and such. For example, competitive ELISA is a preferred cross-blocking assay. Specifically, in a cross-blocking assay, the wells of a microtiter plate are coated with the Prominin-1 protein, which is then pre-incubated with or without a candidate competing antibody, and an anti-Prominin-1 antibody of the present invention is added. The amount of the anti-Prominin-1 antibody of the present invention bound to the Prominin-1 protein in the wells indirectly correlates with the binding ability of the candidate competing antibody (test antibody) that competes for binding to the same epitope. More specifically, with an increasing affinity the test antibody has for the same epitope, there is a decreasing amount of the anti-Prominin-1 antibody of the present invention binding to the Prominin-1 protein-coated wells, and an increasing amount of the test antibody binding to the Prominin-1 protein-coated wells.

The amount of antibody that binds to the wells can be measured easily by labeling the antibody in advance. For example, a biotin-labeled antibody can be measured using an avidin-peroxidase conjugate and suitable substrate. Cross-blocking assays using enzyme labels such as peroxidase are called competitive ELISA assay, in particular. The antibody can be labeled with other detectable or measurable labeling substances. More specifically, radiolabels or fluorescent labels are known.

Furthermore, when the test antibody comprises a constant region derived from a species different from that of the anti-Prominin-1 antibody of the present invention, the amount of antibody bound to the wells can be measured using a labeled antibody that recognizes its constant region. If the antibodies are derived from the same species but belong to different classes, the amount of antibodies bound to the wells can be measured using antibodies that distinctively recognize individual classes.

If a candidate competing antibody can block binding of the anti-Prominin-1 antibody by at least 20%, preferably at least 20% to 50%, and even more preferably at least 50%, as compared to the binding activity obtained in a control experiment performed in the absence of the candidate competing antibody, the candidate competing antibody is either an antibody that binds substantially to the same epitope or one that competes for binding to the same epitope as an anti-Prominin-1 antibody of the present invention.

Specific examples of antibodies that recognize the same epitope as the AC133 antibody include, antibodies comprising the same CDR sequences as those of AC133.

AC133 comprises the amino acid sequence of SEQ ID NO: 12 as a heavy-chain variable region CDR1, the amino acid sequence of SEQ ID NO: 14 as a heavy-chain variable region CDR2, and the amino acid sequence of SEQ ID NO: 16 as a heavy-chain variable region CDR3. Therefore, an embodiment of an antibody of the present invention that recognizes the same epitope as the AC133 antibody is, for example, an antibody comprising the amino acid sequence of SEQ ID NO: 12 as a heavy-chain variable region CDR1, the amino acid sequence of SEQ ID NO: 14 as a heavy-chain variable region CDR2, and the amino acid sequence of SEQ ID NO: 16 as a heavy-chain variable region CDR3.

Furthermore, AC133 comprises the amino acid sequence of SEQ ID NO: 20 as a light-chain variable region CDR1, the amino acid sequence of SEQ ID NO: 22 as a light-chain variable region CDR2, and the amino acid sequence of SEQ ID NO: 24 as a light-chain variable region CDR3. Therefore, an embodiment of an antibody of the present invention that recognizes the same epitope as the AC133 antibody is, for example, an antibody comprising the amino acid sequence of SEQ ID NO: 20 as a light-chain variable region CDR1, the amino acid sequence of SEQ ID NO: 22 as a light-chain variable region CDR2, and the amino acid sequence of SEQ ID NO: 24 as a light-chain variable region CDR3.

In addition, an embodiment of an antibody of the present invention that recognizes the same epitope as AC133 is, for example, an antibody comprising the amino acid sequence of SEQ ID NO: 12 as a heavy-chain variable region CDR1, the amino acid sequence of SEQ ID NO: 14 as a heavy-chain variable region CDR2, the amino acid sequence of SEQ ID NO: 16 as a heavy-chain variable region CDR3, the amino acid sequence of SEQ ID NO: 20 as a light-chain variable region CDR1, the amino acid sequence of SEQ ID NO: 22 as a light-chain variable region CDR2, and the amino acid sequence of SEQ ID NO: 24 as a light-chain variable region CDR3.

Preferred examples of such antibodies include, without particular limitation, chimeric antibodies and humanized antibodies.

An example of a preferred embodiment of the antibody of the present invention includes a chimeric antibody or a humanized antibody.

Chimeric antibody refers to an antibody produced by linking together regions having different origins. Generally, a chimeric antibody is composed of V-regions of an antibody derived from a non-human animal and C regions derived from a human antibody. For example, an antibody comprising the heavy-chain and light-chain variable regions of a mouse antibody and the heavy-chain and light-chain constant regions of a human antibody is a heterologous mouse-human chimeric antibody.

Specific examples of the heavy-chain or light-chain variable regions of a mouse antibody used to produce the chimeric antibody in the present invention include a VH comprising the amino acid sequence of SEQ ID NO: 10 or VL comprising the amino acid sequence of SEQ ID NO: 18. Furthermore, a VH comprising the amino acid sequence encoded by the polynucleotide of SEQ ID NO: 9 or a VL comprising the amino acid sequence encoded by the polynucleotide of SEQ ID NO: 17 may also be included as specific examples of the heavy-chain and light-chain variable regions of the above-mentioned mouse antibody.

On the other hand, a humanized antibody consists of the complementarity determining region (CDR) of an antibody derived from a non-human animal, and the framework region (FR) and C region derived from a human antibody. Since the antigenicity of a humanized antibody in human body is reduced, a humanized antibody is useful as an active ingredient for therapeutic agents of the present invention. A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known.

Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that is highly homologous to a mouse FR is advantageous for maintaining the CDR function. That is, it is generally preferable to use a human FR comprising an amino acid sequence highly homologous to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V-region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After this integration vector is incorporated into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 96/02576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in an FR may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Sato, K. et al., Cancer Res. (1993) 53: 851-856).

Specific examples of the heavy-chain variable region FRs used in the grafting for a humanized antibody of the present invention include the FRs of (1) to (4) below:

(1) FR1 comprising the amino acid sequence of positions 1 to 30 in SEQ ID NO: 32;

(2) FR2 comprising the amino acids of positions 36 to 49 in SEQ ID NO: 32;

(3) FR3 comprising the amino acids of positions 67 to 98 in SEQ ID NO: 32; and (4) FR4 comprising the amino acids of positions 104 to 114 in SEQ ID NO: 32.

Specific examples of the light-chain variable region FRs used in the grafting for a humanized antibody of the present invention include the FRs of (5) to (8) below:

(5) FR1 comprising the amino acid sequence of positions 1 to 23 in SEQ ID NO: 34;

(6) FR2 comprising the amino acid sequence of positions 40 to 54 in SEQ ID NO: 34;

(7) FR3 comprising the amino acid sequence of positions 62 to 93 in SEQ ID NO: 34; and (8) FR4 comprising the amino acid sequence of positions 103 to 112 in SEQ ID NO: 34.

Specific examples of the light-chain variable region FRs used in the grafting for a humanized antibody of the present invention include the FRs of (9) to (12) below:

(9) FR1 comprising the amino acid sequence of positions 1 to 23 in SEQ ID NO: 42;

(10) FR2 comprising the amino acid sequence of positions 40 to 54 in SEQ ID NO: 42;

(11) FR3 comprising the amino acid sequence of positions 62 to 93 in SEQ ID NO: 42; and

(12) FR4 comprising the amino acid sequence of positions 103 to 112 in SEQ ID NO: 42.

Furthermore, specific examples of the light-chain variable region FRs used in the grafting for a humanized antibody of the present invention include the FRs of (13) to (16) below:

(13) FR1 comprising the amino acid sequence of positions 1 to 23 in SEQ ID NO: 46;

(14) FR2 comprising the amino acid sequence of positions 40 to 54 in SEQ ID NO: 46;

(15) FR3 comprising the amino acid sequence of positions 62 to 93 in SEQ ID NO: 46; and

(16) FR4 comprising the amino acid sequence of positions 103 to 112 in SEQ ID NO: 46.

FRs used in the humanized antibodies of the present invention are not limited to the above-mentioned sequences. Furthermore, the FRs of this application also include FR sequences that have one or more amino acid substitutions, deletions, additions, and/or insertions in the amino acid sequence of human FR for improving the functions of the humanized antibodies.

An example of a preferred embodiment of an antibody of the present invention includes an antibody whose heavy-chain constant region is not mouse IgG1. Antibodies that are not mouse IgG1 include without particular limitation, for example, mouse IgG2a, mouse IgG2b, mouse IgG3, human IgG1, human IgG2, human IgG3, and human IgG4. A preferred subtype in the present invention is human IgG1. The light chain is not particularly limited, and may be a κ chain or λ chain, but κ chain is preferred and a human κ chain is particularly preferred.

An example of a preferred embodiment of an antibody of the present invention includes an antibody not bound with a cytotoxic substance. Cytotoxic substances are substances that induce cell death, and are specifically toxins, radioactive substances, or chemotherapeutic agents. Specific examples of toxins include the following: Diphtheria toxin A chain (Langone J. J., et al., Methods in Enzymology (1983) 93: 307-308); *Pseudomonas* Exotoxin (Nature Medicine (1996) 2: 350-353); Ricin A Chain (Fulton R. J. et al., J. Biol. Chem. (1986) 261: 5314-5319; Sivam G., et al., Cancer Res. (1987) 47: 3169-3173; Cumber A. J. et al., J. Immunol. Methods (1990) 135: 15-24; Wawrzynczak E. J., et al., Cancer Res. (1990) 50: 7519-7562; Gheeite V., et al., J. Immunol. Methods (1991) 142: 223-230); Deglicosylated Ricin A Chain (Thorpe P. E., et al., Cancer Res. (1987) 47: 5924-5931); Abrin A Chain (Wawrzynczak E. J., et al., Br. J. Cancer (1992) 66: 361-366; Wawrzynczak E. J., et al., Cancer Res. (1990) 50: 7519-7562; Sivam G., et al., Cancer Res. (1987) 47: 3169-3173; Thorpe P. E. et al., Cancer Res. (1987) 47: 5924-5931); Gelonin (Sivam G., et al., Cancer Res. (1987) 47: 3169-3173; Cumber A. J., et al., J. Immunol. Methods (1990) 135: 15-24; Wawrzynczak E. J., et al., Cancer Res. (1990) 50: 7519-7562; Bolognesi A., et al., Clin. Exp. Immunol. (1992) 89: 341-346); Pokeweed anti-viral protein fromseeds (PAP-s) (Bolognesi A., et al., Clin. Exp. Immunol. (1992) 89: 341-346); Briodin (Bolognesi A., et al., Clin. Exp. Immunol. (1992) 89: 341-346); Saporin (Bolognesi A., et al., Clin. Exp. Immunol. (1992) 89: 341-346); Momordin (Cumber A., et al., J. Immunol. Methods (1990) 135: 15-24; Wawrzynczak E. J., et al., Cancer Res. (1990) 50: 7519-7562; Bolognesi A., et al., Clin. Exp. Immunol. (1992) 89: 341-346); Momorcochin (Bolognesi A., et al., Clin. Exp. Immunol., (1992) 89: 341-346); Dianthin 32 (Bolognesi A., et al., Clin. Exp. Immunol. (1992) 89: 341-346); Dianthin 30 (Stirpe F., Barbieri L., FEBS letter (1986) 195: 1-8); Modeccin (Stirpe F., Barbieri L., FEBS letter (1986) 195: 1-8); Viscumin (Stirpe F., Barbieri L., FEBS letter (1986) 195: 1-8); Volkesin (Stirpe F., Barbieri L., FEBS letter (1986) 195: 1-8); Dodecandrin (Stirpe F., Barbieri L., FEBS letter (1986) 195: 1-8); Tritin (Stirpe F., Barbieri L., FEBS letter (1986) 195: 1-8); Luffin (Stirpe F., Barbieri L., FEBS letter (1986) 195: 1-8); Trichokirin (Casellas P., et al., Eur. J. Biochem. (1988) 176: 581-588; Bolognesi A., et al., Clin. Exp. Immunol., (1992) 89: 341-346).

Radioactive substances refer to substances containing a radioisotope, and include $^{32}P$, $^{14}C$, $^{125}I$, $^{3}H$, $^{131}I$, $^{186}Re$, and $^{188}Re$.

Chemotherapeutic agents include cytokines, anti-tumor agents, and enzymes. Chemotherapeutic agents usually have a molecular weight of 200 to 1,000. Examples of chemotherapeutic agents include the following substances: monomethyl auristatin F (MMAF), Melphalan (Rowland G. F., et al., Nature (1975) 255: 487-488); Cis-platinum (Hurwitz E. and Haimovich J., Method In Enzymology (1986) 178: 369-375; Schechter B., et al., Int. J. Cancer (1991) 48: 167-172); Carboplatin (Ota, Y., et al., Asia-Oceania J. Obstet. Gynaecol. (1993) 19: 449-457); Mitomycin C (Noguchi, A., et al., Bioconjugate Chem. (1992) 3: 132-137); Adriamycin (Doxorubicin) (Shih, L. B., et al., Cancer Res. (1991) 51: 4192-4198; Zhu, Z., et al., Cancer Immunol. Immumother (1995) 40: 257-267; Trail, P. A., et al., Science (1993) 261: 212-215; Kondo, Y., et al., Jpn. J. Cancer Res. (1995) 86: 1072-1079); Daunorubicin (Dillman, R. O., et al., Cancer Res. (1988) 48: 6097-6102; Hudecz, F., et al., Bioconjugate Chem. (1990) 1: 197-204; Tukada Y. et al., J. Natl. Cancer Inst. (1984) 75: 721-729); Bleomycin (Manabe, Y., et al., Biochem. Biophys. Res. Commun. (1983) 115: 1009-1014); Neocarzinostatin (Kitamura K., et al., Cancer Immunol. Immumother (1993) 36: 177-184; Yamaguchi T., et al., Jpn. J. Cancer Res. (1994) 85: 167-171); Methotrexate (Kralovec, J., et al., Cancer Immunol. Immumother (1989) 29: 293-302; Kulkarni, P. N., et al., Cancer Res. (1981) 41: 2700-2706; Shin, L. B., et al., Int. J. Cancer (1988) 41: 832-839; Gamett M. C., et al., Int. J. Cancer (1983) 31: 661-670); 5-Fluorouridine (Shin, L. B., Int. J. Cancer (1990) 46: 1101-1106); 5-Fluoro-2'-deoxyuridine (Goerlach A., et al., Bioconjugate Chem. (1991) 2: 96-101); Cytosine arabinoside (Hurwitz E., et al., J. Med. Chem. (1985) 28: 137-140); Aminopterin (Kanellos J., et al., Immunol. Cell Biol. (1987) 65: 483-493); Vincristine (Johnson J. R., et al., Br. J. Cancer (1980) 42: 17); Vindesine (Johnson J. R., et al., Br. J. Cancer (1981) 44: 472-475); Interleukin 2 (IL-2), Tumor necrosis factor α (TNF-α), Interferon (IFN), Carboxypeptidase, Alkaline phosphatase, β-lactamase, Cytidine deaminase.

Antibodies of the present invention may be antibodies with a modified sugar chain. It is known that cytotoxic activity of an antibody can be increased by modifying its sugar chain.

Examples of antibodies having modified sugar chains include glycosylated antibodies (for example, WO 99/54342), antibodies with defucosylated sugar chain (for example, WO 00/61739, WO 02/31140, WO 2006/067847, and WO 2006/067913), and antibodies having a sugar chain with bisecting GlcNAc (for example, WO 02/79255).

Preferred sugar chain-modified antibodies of the present invention include defucosylated antibodies. Sugar chains that are linked to an antibody include N-glycoside-linked sugar chains, which are attached to a nitrogen atom on the side chain of an asparagine residue on the antibody molecule, and β-glycosyl-linked sugar chains, which are attached to a hydroxyl group on the side chain of a serine or threonine residue on the antibody molecule, and the sugar chains for which the presence or absence of fucose is concerned in the present invention are the N-glycoside-linked sugar chains.

"Defucosylated antibodies" in the present invention means that of the N-glycoside-linked sugar chains of antibodies in a composition, 20% or more, preferably 50% or more, more preferably 70% or more, and even more preferably 90% or more of the N-glycoside-linked sugar chains are defucosylated.

Defucosylated antibodies can be produced by methods known to those skilled in the art, and for example, they can be produced by expressing the antibodies in host cells which have no or low ability to add α-1,6 core fucose. Host cells which have no or low ability to add fucose are not particularly limited, but examples include rat myeloma YB2/3HL.P2.G11.16Ag.20 cell (abbreviated as YB2/0 cells) (stored as ATCC CRL 1662), FTVIII knock-out CHO cell (WO 02/31140), Lec13 cell (WO 03/035835), and fucose transporter-deficient cell (WO 2006/067847 and WO 2006/067913).

Analysis of sugar chains can be performed by methods known to those skilled in the art. For example, N-Glycosidase F (Roche) or the like is reacted with the antibody to release sugar chains from the antibody. Then, after desalting by solid-phase extraction using a cellulose cartridge (Shimizu Y. et al., Carbohydrate Research (2001) 332: 381-388), concentration to dryness is followed by fluorescence labeling with 2-aminopyridine (Kondo A. et al., Agricultural and Biological Chemistry (1990) 54 (8): 2169-2170). After reagents were removed from the obtained pyridylaminated sugar chains by solid-phase extraction using a cellulose cartridge, the resulting material was concentrated by centrifugation to prepare purified pyridylaminated sugar chains. Then, measurements can be made by performing reverse-phase HPLC analysis using an ODS column. After pyridylaminated sugar chains are prepared, measurements can be made by performing a two-dimensional mapping that combines reverse phase HPLC analysis with an ODS column and a normal phase HPLC analysis with an amino column.

The antibody of the present invention is not limited to the whole antibody molecule, but includes minibodies or modified products thereof as long as they bind to the Prominin-1 protein.

A minibody contains an antibody fragment lacking a portion of a whole antibody (for example, whole IgG). As long as it has the ability to bind the Prominin-1 antigen, partial deletions of an antibody molecule are acceptable. Antibody fragments of the present invention preferably contain a heavy-chain variable region (VH) and/or a light-chain variable region (VL). The amino acid sequence of VH or VL may contain substitutions, deletions, additions, and/or insertions.

Furthermore, as long as it has the ability to bind the Prominin-1 antigen, VH and/or VL can be partially deleted. The variable region may be chimerized or humanized. Specific examples of the antibody fragments include Fab, Fab', $F(ab')_2$, and Fv. Specific examples of minibodies include Fab, Fab', $F(ab')_2$, Fv, scFv (single chain Fv), diabody, and $sc(Fv)_2$ (single chain $(Fv)_2$). Multimers of these antibodies (for example, dimers, trimers, tetramers, and polymers) are also included in the minibodies of the present invention.

Furthermore, the antibody of the present invention may be a bispecific antibody. A bispecific antibody refers to an antibody that carries variable regions that recognize different epitopes within the same antibody molecule but the epitopes may be present in separate molecules or in the same molecule. That is, in the present invention, the bispecific antibody may have antigen-binding sites that recognize different epitopes on a Prominin-1 protein. Two molecules of such a bispecific antibody can bind to one molecule of Prominin-1. As a result, stronger cytotoxic activity can be expected. "Antibodies" in the present invention also include these antibodies.

Furthermore, in the present invention, bispecific antibodies that recognize antigens other than Prominin-1 may be combined. For example, it is possible to combine bispecific antibodies that recognize non-Prominin-1 antigens that are specifically expressed on the surface of target cancer cells like Prominin-1.

Methods for producing bispecific antibodies are known. For example, two types of antibodies recognizing different antigens may be linked to prepare a bispecific antibody. The antibodies to be linked may be half molecules each having an H chain or an L chain, or may be quarter molecules consisting of only an H chain. Alternatively, bispecific antibody-producing fused cells can be prepared by fusing hybridomas producing different monoclonal antibodies. Bispecific antibodies can also be prepared by genetic engineering techniques.

In particular, monoclonal antibodies derived from a mammal are examples of the preferred embodiments of the anti-Prominin-1 antibodies of the present invention. Anti-Prominin-1 monoclonal antibodies can be obtained using known means. The monoclonal antibodies derived from a mammal include antibodies produced by hybridoma, and antibodies produced by a host transformed by genetic engineering techniques with an expression vector containing an antibody gene.

A monoclonal antibody-producing hybridoma can be prepared essentially by using the known technique below. More specifically, immunization is performed using the Prominin-1 protein or Prominin-1-expressing cells as a sensitizing antigen according to a conventional immunization method. The obtained immunocytes are then fused to known parent cells by a conventional cell fusion method, and then monoclonal antibody-producing cells are screened by a common screening method to prepare the hybridoma.

Specifically, monoclonal antibodies are prepared as follows.

First, Prominin-1 protein for use as the sensitizing antigen for obtaining antibodies is obtained. Specifically, the Prominin-1-encoding nucleotide sequence is inserted into a known expression vector system to transform an appropriate host cell, and then the human Prominin-1 protein of interest is purified by a known method from the host cell or its culture supernatant.

Then, this purified Prominin-1 protein is used as a sensitizing antigen. Alternatively, a partial peptide of Prominin-1 can be used as a sensitizing antigen. In this case, the partial peptide can be obtained from the amino acid sequence of human Prominin-1 by chemical synthesis.

The epitope on Prominin-1 molecule recognized by an anti-Prominin-1 antibody of the present invention is not particularly limited, and any epitope may be recognized as long as it is an epitope on the Prominin-1 molecule. Therefore, as an antigen for producing anti-Prominin-1 antibodies of the present invention, any fragment may be used so long as it is a fragment containing an epitope present on the Prominin-1 molecule.

There is no limitation as to the type of mammalian species to be immunized with the sensitizing antigen. However, a mammal is preferably selected based on its compatibility with the parental cell to be used in cell fusion. Generally, rodents (for example, mice, rats, and hamsters), rabbits, monkeys, and the like can be used.

Animals can be immunized with a sensitized antigen by known methods such as a routine method of injecting a sensitized antigen into a mammal intraperitoneally or subcutaneously. Specifically, the sensitized antigen is diluted appropriately with phosphate-buffered saline (PBS), physiological saline and such, and then suspended. An adequate amount of a conventional adjuvant, for example, Freund's complete adjuvant, is mixed with the suspension, as necessary. An emulsion is then prepared for administering to a mammal several times over a 4- to 21-day interval. An appropriate carrier may be used for the sensitized antigen in immunization.

A mammal is immunized as described above. After a titer increase of target antibody in the serum is confirmed, immunocytes are collected from the mammal and then subjected to cell fusion. Spleen cells are the preferred immunocytes.

Mammalian myeloma cells are used as the parental cells to be fused with the above immunocytes. Preferable myeloma cells to be used include various known cell lines, for example, P3 (P3x63Ag8.653) (J. Immunol. (1979) 123: 1548-1550), P3x63Ag8U.1 (Current Topics in Microbiology and Immunology (1978) 81: 1-7), NS-1 (Kohler, G. and Milstein, C. Eur. J. Immunol. (1976) 6: 511-519), MPC-11 (Margulies, D. H. et al., Cell (1976) 6: 405-415), SP2/0 (Shulman, M. et al., Nature (1978) 276: 269-270), FO (deSt. Groth, S. F. et al., J. Immunol. Methods (1980) 35: 1-21), 5194 (Trowbridge, I. S., J. Exp. Med. (1978) 148: 313-323), and 8210 (Galfre, G. et al., Nature (1979) 277: 131-133).

Cell fusions between the immunocytes and the myeloma cells as described above can be essentially carried out using known methods, for example, a method by Kohler and Milstein (Kohler, G. and Milstein, C., Methods Enzymol. (1981) 73: 3-46).

More specifically, the above-described cell fusions are carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide may also be added to improve fusion efficiency.

The ratio of immunocytes to myeloma cells may be determined at one's own discretion, preferably, for example, one myeloma cell for every one to ten immunocytes. Culture media to be used for the above cell fusions include, for example, media that are suitable for the growth of the above myeloma cell lines, such as RPMI1640 medium and MEM medium, and other conventional culture medium used for this type of cell culture. In addition, serum supplements such as fetal calf serum (FCS) may also be used in combination.

Cell fusion is carried out as follows. As described above, predetermined amounts of immunocytes and myeloma cells are mixed well in the culture medium. PEG solution (for example, mean molecular weight of about 1,000-6,000) preheated to 37° C. is added to the cell suspension typically at a concentration of 30% to 60% (w/v), and mixed to produce fused cells (hybridomas). Then, an appropriate culture medium is successively added to the mixture, and the sample is centrifuged to remove supernatant. This treatment is repeated several times to remove the unwanted cell fusion-promoting agent and others that are unfavorable to hybridoma growth.

Screening of the resulting hybridomas can be carried out by culturing them in a conventional selective medium, for example, hypoxanthine, aminopterin, and thymidine (HAT) medium. Culturing in the above-descried HAT medium is continued for a period long enough (typically, for several days to several weeks) to kill cells (non-fused cells) other than the desired hybridomas. Then, hybridomas are screened for single-cell clones capable of producing the target antibody by conventional limiting dilution methods.

In addition to the method for preparing the above-described hybridomas by immunizing non-human animals with antigens, preferred human antibodies having binding activity to Prominin-1 can also be obtained by: sensitizing human lymphocytes with Prominin-1 in vitro; and fusing the sensitized lymphocytes with human myeloma cells capable of dividing permanently (see, Japanese Patent Application Kokoku Publication No. (JP-B) H01-59878 (examined, approved Japanese patent application published for opposition)). Alternatively, it is possible to obtain human antibodies against Prominin-1 from immortalized cells producing anti-Prominin-1 antibodies. In this method, the cells producing anti-Prominin-1 antibodies are prepared by administering Prominin-1 as an antigen to transgenic animals comprising a repertoire of the entire human antibody genes (see, WO 94/25585, WO 93/12227, WO 92/03918, and WO 94/02602).

The monoclonal antibody-producing hybridomas thus prepared can be passaged in a conventional culture medium, and stored in liquid nitrogen over long periods of time.

Monoclonal antibodies can be prepared from the above-described hybridomas by, for example, a routine procedure of culturing the hybridomas and obtaining antibodies from the culture supernatants. Alternatively, monoclonal antibodies can be prepared by injecting the hybridomas into a compatible mammal; growing these hybridomas in the mammal; and obtaining antibodies from the mammal's ascites. The former method is suitable for preparing highly purified antibodies, while the latter is suitable for preparing antibodies on a large scale.

Recombinant antibodies can also be prepared by: cloning an antibody gene from a hybridoma; inserting the gene into an appropriate vector; introducing the vector into a host; and producing the antibodies by using genetic recombination techniques (see, for example, Vandamme, A. M. et al., Eur. J. Biochem. (1990) 192: 767-775).

Specifically, an mRNA encoding the variable (V) region of anti-Prominin-1 antibody is isolated from hybridomas producing the anti-Prominin-1 antibodies. For mRNA isolation, total RNAs are first prepared by conventional methods such as guanidine ultracentrifugation methods (Chirgwin, J. M. et al., Biochemistry (1979) 18: 5294-5299), or acid guanidinium thiocyanate-phenol-chloroform (AGPC) methods (Chomczynski, P. et al., Anal. Biochem. (1987) 162: 156-159), and then the target mRNA is prepared using an mRNA Purification Kit (Pharmacia) and such. Alternatively, the mRNA can be directly prepared using the QuickPrep mRNA Purification Kit (Pharmacia).

A cDNA of the antibody V region is synthesized from the resulting mRNA using reverse transcriptase. cDNA synthesis is carried out using the AMV Reverse Transcriptase First-strand cDNA Synthesis Kit (Seikagaku Co.), or such. Alternatively, cDNA can be synthesized and amplified by the 5'-RACE method (Frohman, M. A. et al., Proc. Natl. Acad. Sci. USA (1988) 85: 8998-9002; Belyaysky, A. et al., Nucleic Acids Res. (1989) 17: 2919-2932) using the 5'-Ampli FINDER RACE Kit (Clontech) and PCR.

Target DNA fragments are purified from the obtained PCR products and then ligated with vector DNAs to prepare recombinant vectors. The vectors are introduced into *E. coli* and such, and colonies are selected for preparing the recombinant vector of interest. The target DNA nucleotide sequence is then confirmed by conventional methods such as the dideoxynucleotide chain termination method.

Once a DNA encoding the V region of target anti-Prominin-1 antibody is obtained, the DNA is inserted into an expression vector which comprises a DNA encoding the constant region (C region) of a desired antibody.

To produce an anti-Prominin-1 antibody for use in the present invention, generally, the antibody gene is incorporated into an expression vector so that it is expressed under the regulation of an expression regulatory region, for example, an enhancer or a promoter. Then, antibodies are expressed by transforming host cells with this expression vector.

For expressing the antibody gene, polynucleotides encoding H chain and L chain, respectively, are inserted into separate expression vectors and co-transfected into a host cell. Alternatively, polynucleotides encoding both H chain and L chain are inserted into a single expression vector and transfected into a host cell (see WO 94/11523).

Specific examples of the antibodies of the present invention include chimeric antibodies having constant regions such as those below. Further examples include antibodies comprising amino acid sequences of these constant regions with one or more amino acid substitutions, deletions, additions, and/or insertions, and having equivalent activity to these chimeric antibodies, but the present invention is not limited to these antibodies.

(a) A chimeric antibody whose heavy chain constant region is mouse IgG2a (heavy chain nucleotide sequence, SEQ ID NO: 1; heavy chain amino acid sequence, SEQ ID NO: 2; and amino acids 1 to 19 correspond to the signal sequence).

(b) A chimeric antibody whose light chain constant region is mouse Igκ (light chain nucleotide sequence, SEQ ID NO: 3; light chain amino acid sequence, SEQ ID NO: 4; and amino acids 1 to 20 correspond to the signal sequence).

(c) A human chimeric antibody whose heavy chain constant region is human IgG1 (heavy chain nucleotide sequence, SEQ ID NO: 5; heavy chain amino acid sequence, SEQ ID NO: 6; and amino acids 1 to 19 correspond to the signal sequence).

(d) A human chimeric antibody whose light chain constant region is human Igκ (light chain nucleotide sequence, SEQ ID NO: 7; light chain amino acid sequence, SEQ ID NO: 8; and amino acids 1 to 20 correspond to the signal sequence).

Specific examples of the antibodies of the present invention include but are not limited to humanized antibodies such as those below.

(i) A humanized antibody wherein the amino acid at position 15 in a light-chain variable region FR1 which corresponds to position 15 in the amino acid sequence of SEQ ID NO: 34 is Phe.

(ii) A humanized antibody wherein the amino acid at position 15 in a light-chain variable region FR1 which corresponds to position 15 in the amino acid sequence of SEQ ID NO: 34 is Phe, and the amino acid at position 18 in a light-chain variable region FR1 which corresponds to position 18 in the amino acid sequence of SEQ ID NO: 34 is Gln.

Without particular limitation, the above-mentioned antibodies preferably comprise the amino acid sequence of SEQ ID NO: 12 as a heavy-chain variable region CDR1, the amino acid sequence of SEQ ID NO: 14 as a heavy-chain variable region CDR2, and the amino acid sequence of SEQ ID NO: 16 as a heavy-chain variable region CDR3. Furthermore, they preferably comprise the amino acid sequence of SEQ ID NO: 20 as a light-chain variable region CDR1, the amino acid sequence of SEQ ID NO: 22 as a light-chain variable region CDR2, and the amino acid sequence of SEQ ID NO: 24 as a light-chain variable region CDR3.

Furthermore, specific examples of the antibodies of the present invention include humanized antibodies such as those below, but the present invention is not limited to these antibodies.

(1) A humanized antibody whose heavy chain is a humanized antibody H chain (h133H) (heavy chain nucleotide sequence, SEQ ID NO: 31; heavy chain amino acid sequence, SEQ ID NO: 32; and amino acids −19 to −1 correspond to the signal sequence).

(2) A humanized antibody whose light chain is a humanized antibody L chain (h133L) (light chain nucleotide sequence, SEQ ID NO: 33; light chain amino acid sequence, SEQ ID NO: 34; and amino acids −22 to −1 correspond to the signal sequence).

(3) A humanized antibody whose light chain is a humanized antibody L chain (hybrid L1) carrying the FR1 mouse sequence (the signal sequence is also derived from a mouse antibody sequence) (light chain nucleotide sequence, SEQ ID NO: 35; light chain amino acid sequence, SEQ ID NO: 36; and amino acids −20 to −1 correspond to the signal sequence).

(4) A humanized antibody whose light chain is a humanized antibody L chain (hybrid L2) carrying the FR1 humanized sequence (the signal sequence is also derived from a humanized antibody sequence) (light chain nucleotide sequence, SEQ ID NO: 37; light chain amino acid sequence, SEQ ID NO: 38; and amino acids −22 to −1 correspond to the signal sequence).

(5) A humanized antibody whose light chain is a humanized antibody L chain (h133L (b)) (light chain nucleotide sequence, SEQ ID NO: 39; light chain amino acid sequence, SEQ ID NO: 40; and amino acids −22 to −1 correspond to the signal sequence).

(6) A humanized antibody whose light chain is a humanized antibody L chain (h133L (c)) (light chain nucleotide sequence, SEQ ID NO: 41; light chain amino acid sequence, SEQ ID NO: 42; and amino acids −22 to −1 correspond to the signal sequence).

(7) A humanized antibody whose light chain is a humanized antibody L chain (h133L (d)) (light chain nucleotide sequence, SEQ ID NO: 43; light chain amino acid sequence, SEQ ID NO: 44; and amino acids −22 to −1 correspond to the signal sequence).

(8) A humanized antibody whose light chain is a humanized antibody L chain (h133L (e)) (light chain nucleotide sequence, SEQ ID NO: 45; light chain amino acid sequence, SEQ ID NO: 46; and amino acids −22 to −1 correspond to the signal sequence).

(9) A humanized antibody whose light chain is a humanized antibody L chain (h133L (f)) (light chain nucleotide sequence, SEQ ID NO: 47; light chain amino acid sequence, SEQ ID NO: 48; and amino acids −22 to −1 correspond to the signal sequence).

(10) A humanized antibody whose light chain is a humanized antibody L chain (h133L (g)) (light chain nucleotide sequence, SEQ ID NO: 49; light chain amino acid sequence, SEQ ID NO: 50; and amino acids −22 to −1 correspond to the signal sequence).

(11) A humanized antibody whose light chain is a humanized antibody L chain (h133L (h)) (light chain nucleotide sequence, SEQ ID NO: 51; light chain amino acid sequence, SEQ ID NO: 52; and amino acids −22 to −1 correspond to the signal sequence).

(12) A humanized antibody comprising the H chain of (1) (h133H) and the L chain of (6) (h133L (c)).

(13) A humanized antibody comprising the H chain of (1) (h133H) and the L chain of (8) (h133L (e)).

(14) A humanized antibody comprising a heavy chain variable region (h133VH) comprising the amino acid sequence of positions 1 to 114 of SEQ ID NO: 32.

(15) A humanized antibody comprising a light chain variable region (h133VL) comprising the amino acid sequence of positions 1 to 112 of SEQ ID NO: 34.

(16) A humanized antibody comprising a light chain variable region (hybrid L1) comprising the amino acid sequence of positions 1 to 112 of SEQ ID NO: 36.

(17) A humanized antibody comprising a light chain variable region (hybrid L2) comprising the amino acid sequence of positions 1 to 112 of SEQ ID NO: 38.

(18) A humanized antibody comprising a light chain variable region (h133VL (b)) comprising the amino acid sequence of positions 1 to 112 of SEQ ID NO: 40.

(19) A humanized antibody comprising a light chain variable region (h133VL (c)) comprising the amino acid sequence of positions 1 to 112 of SEQ ID NO: 42.

(20) A humanized antibody comprising a light chain variable region (h133VL (d)) comprising the amino acid sequence of positions 1 to 112 of SEQ ID NO: 44.

(21) A humanized antibody comprising a light chain variable region (h133VL (e)) comprising the amino acid sequence of positions 1 to 112 of SEQ ID NO: 46.

(22) A humanized antibody comprising a light chain variable region (h133VL (f)) comprising the amino acid sequence of positions 1 to 112 of SEQ ID NO: 48.

(23) A humanized antibody comprising a light chain variable region (h133VL (g)) comprising the amino acid sequence of positions 1 to 112 of SEQ ID NO: 50.

(24) A humanized antibody comprising a light chain variable region (h133VL (h)) comprising the amino acid sequence of positions 1 to 112 of SEQ ID NO: 52.

(25) A humanized antibody comprising the heavy chain variable region of (14) and the light chain variable region of (19).

(26) A humanized antibody comprising the heavy chain variable region of (14) and the light chain variable region of (21).

(27) A humanized antibody functionally equivalent to the antibody of any of (1) to (26).

Herein, the term "functionally equivalent" means that the antibody of interest has biological or biochemical activity equivalent to an antibody of the present invention. Examples of such activity include binding activity, ADCC activity, or CDC activity.

In the present invention, "equivalent" does not necessarily have to be the same degree of activity, and the activity may be enhanced or reduced as long as the activity is sustained. An antibody with reduced activity is for example, an antibody whose activity is 30% or more, preferably 50% or more, or more preferably 80% or more of that of the original antibody.

Methods for preparing polypeptides functionally equivalent to a certain polypeptide are well known to those skilled in the art, and include methods of introducing mutations into polypeptides. For example, those skilled in the art can prepare an antibody functionally equivalent to the antibodies of the present invention by introducing appropriate mutations into the antibody using site-directed mutagenesis (Hashimoto-Gotoh, T. et al. Gene (1995) 152: 271-275; Zoller, M J, and Smith, M. Methods Enzymol. (1983) 100: 468-500; Kramer, W. et al., Nucleic Acids Res. (1984) 12: 9441-9456; Kramer, W. and Fritz H J, Methods Enzymol. (1987) 154: 350-367; Kunkel, T A, Proc. Natl. Acad. Sci. USA (1985) 82: 488-492; Kunkel, Methods Enzymol. (1988) 85: 2763-2766), or such. Amino acid mutations may occur naturally. Thus, the present invention also comprises antibodies functionally equivalent to the antibodies of the present invention and comprising the amino acid sequences of these antibodies, in which one or more amino acids is mutated. In such mutants, the number of amino acids that may be mutated is not particularly restricted, so long as the activity is maintained. Generally, the number of amino acids that are mutated is 50 amino acids or less, preferably 30 or less, more preferably 10 or less (for example, five amino acids or less). Likewise, the site of mutation is not particularly restricted, so long as the mutation does not result in the disruption of activity.

Amino acid mutations may be made at one or more predicted, preferably nonessential, amino acid residues. A "nonessential" amino acid residue is a residue that can be altered from the wild-type sequence of a protein without altering the biological activity, whereas an "essential" amino acid residue is required for biological activity. An amino acid is preferably substituted for a different amino acid(s) that allows the properties of the amino acid side-chain to be conserved. Accordingly, throughout the present application, a "conservative amino acid substitution" means a replacement of an amino acid residue belonging to one of the following groups with another amino acid in the same group having a chemically similar side chain. Groups of amino acid residues having similar side chains have been defined in the art. Examples of amino acid side chain properties are: hydrophobic amino acids (A, I, L, M, F, P, W, Y, and V), hydrophilic amino acids (R, D, N, C, E, Q, G, H, K, S, and T), amino acids comprising the following side chains: aliphatic side chains (G, A, V, L, I, and P); hydroxyl-containing side chains (S, T, and Y); sulfur-containing side chains (C and M); carboxylic acid- and amide-containing side chains (D, N, E, and Q); basic side chains (R, K, and H); aromatic ring-containing side chains (H, F, Y, and W) (amino acids are represented by one-letter codes in parentheses).

A polypeptide comprising a modified amino acid sequence, in which one or more amino acid residues is deleted, added, and/or replaced with other amino acids, is known to retain its original biological activity (Mark, D. F. et al., Proc. Natl. Acad. Sci. USA (1984) 81: 5662-5666; Zoller, M. J. & Smith, M. Nucleic Acids Research (1982) 10: 6487-6500; Wang, A. et al., Science 224: 1431-1433; Dalbadie-McFarland, G. et al., Proc. Natl. Acad. Sci. USA (1982) 79: 6409-6413).

The present invention also provides polynucleotides encoding the above-mentioned chimeric antibodies, and polynucleotides that hybridize under stringent conditions to these polynucleotides and encode antibodies having an activity equivalent to that of the antibodies of the present invention. The polynucleotides of the present invention are polymers comprising multiple nucleic bases or base pairs of deoxyribonucleic acids (DNAs) or ribonucleic acids (RNAs), and are not particularly limited, as long as they encode the antibodies of the present invention. Non-natural nucleotides may also be included. The polynucleotides of the present invention can be used to express antibodies using genetic engineering techniques. Furthermore, they can be used as probes in the screening of antibodies functionally equivalent to the antibodies of the present invention. Specifically, DNAs that hybridize under stringent conditions to the polynucleotides encoding the antibodies of the present invention, and encode antibodies having an activity equivalent to that of the antibodies of the present invention, can be obtained by techniques such as hybridization and gene amplification (for example, PCR), using a polynucleotide of the present invention or a portion thereof as a probe. Such DNAs are also included in the polynucleotides of the present invention. Hybridization techniques are well known to those skilled in the art (Sambrook, J. et al., Molecular Cloning 2nd ed., 9.47-9.58, Cold Spring Harbor Lab. press, 1989). In one example, hybridization is performed by conducting prehybridization at 42° C. overnight in a hybridization solution comprising 25% formamide or 50% formamide under more stringent conditions, 4×SSC, 50 mM Hepes pH 7.0, 10×Denhardt's solution, and 20 ng/mL denatured salmon sperm DNA, then adding a labeled probe, and warming at 42° C. overnight. The subsequent wash can be carried out using a washing solution and temperature conditions of "1×SSC, 0.1% SDS, 37° C." and such, more stringently "0.5×SSC, 0.1% SDS, 42° C." and such, or even more stringently "0.2×SSC, 0.1% SDS, 65° C." and such. This way, as the washing conditions for hybridization become more stringent, DNA having higher homology to the probe sequence is expected to be isolated. However, the above-mentioned combination of SSC, SDS, and temperature conditions are examples, and those skilled in the art can suitably combine the above-mentioned factors that determine the hybridization stringency or other factors (for example, probe concentration, probe length, and hybridization reaction time) to realize similar stringencies.

Antibodies that are encoded by polynucleotides obtained by the hybridization and gene amplification techniques, and are functionally equivalent to the antibodies of the present invention generally exhibit high homology to the antibodies of the this invention at the amino acid level. The antibodies of the present invention include antibodies that are functionally equivalent to the antibodies of the present invention, and exhibit high amino acid sequence homology to the antibodies of this invention. The term "high homology" generally means identity at the amino acid level of at least 50% or higher, preferably 75% or higher, more preferably 85% or higher, still more preferably 95% or higher. Polypeptide homology can be determined by the algorithm described in the report: Wilbur, W. J. and Lipman, D. J. Proc. Natl. Acad. Sci. USA (1983) 80: 726-730.

The present invention provides pharmaceutical compositions comprising the above-mentioned anti-Prominin-1 antibodies as an active ingredient. The present invention also relates to anticancer agents comprising the above-mentioned anti-Prominin-1 antibodies as an active ingredient. The anticancer agents of the present invention are preferably administered to subjects affected by cancer or subjects with the possibility of cancer recurrence.

In the present invention, an anticancer agent comprising an anti-Prominin-1 antibody as an active ingredient can also be described as a method for preventing or treating cancer which comprises the step of administering an anti-Prominin-1 antibody to a subject, or as use of an anti-Prominin-1 antibody in the manufacturing of an anticancer agent.

The type of cancer treated by the anticancer agents of the present invention is not particularly limited, but is generally cancers expressing the Prominin-1 protein, and preferably cancers with cancer stem cells. Examples of cancers expressing the Prominin-1 protein include colon cancer, breast cancer, brain tumor, ependymoma, stomach cancer, pancreatic cancer, liver cancer, kidney cancer, prostate cancer, and blood tumor (AML and CLL).

In the present invention, the phrase "comprising an anti-Prominin-1 antibody as an active ingredient" means comprising an anti-Prominin-1 antibody as the main active component, and does not limit the content percentage of the monoclonal antibody.

Furthermore, multiple types of antibodies can be mixed as necessary with a pharmaceutical composition or anticancer agent in the present invention. For example, by forming a cocktail of multiple anti-Prominin-1 antibodies, cytotoxic effect against Prominin-1-expressing cells may be enhanced. Alternatively, therapeutic effects can be enhanced by mixing other antibodies that recognize tumor-related antigens in addition to anti-Prominin-1 antibodies.

The pharmaceutical compositions or anticancer agents of the present invention can be administered orally or parenterally to a patient. Preferably, the administration is parenteral administration. Specifically, the method of administration is, for example, administration by injection, transnasal administration, transpulmonary administration, or transdermal administration. Examples of administration by injection include systemic and local administrations of a pharmaceutical composition of the present invention by intravenous injection, intramuscular injection, intraperitoneal injection, subcutaneous injection, or such. A suitable administration method may be selected according to the age of the patient and symptoms. The dosage may be selected, for example, within the range of 0.0001 mg to 1,000 mg per kg body weight in each administration. Alternatively, for example, the dosage for each patient may be selected within the range of 0.001 to 100,000 mg/body. However, the pharmaceutical composition of the present invention is not limited to these doses.

The pharmaceutical compositions of the present invention can be formulated according to conventional methods (for example, Remington's Pharmaceutical Science, latest edition, Mark Publishing Company, Easton, U.S.A.), and may also contain pharmaceutically acceptable carriers and additives. Examples include, but are not limited to, surfactants, excipients, coloring agents, flavoring agents, preservatives, stabilizers, buffers, suspension agents, isotonic agents, binders, disintegrants, lubricants, fluidity promoting agents, and corrigents, and other commonly used carriers can be suitably used. Specific examples of the carriers include light anhydrous silicic acid, lactose, crystalline cellulose, mannitol, starch, carmellose calcium, carmellose sodium, hydroxypropyl cellulose, hydroxypropyl methyl cellulose, polyvinylacetal diethylaminoacetate, polyvinylpyrrolidone, gelatin, medium chain fatty acid triglyceride, polyoxyethylene hardened castor oil 60, saccharose, carboxymethyl cellulose, corn starch, inorganic salt, and such.

The present invention provides methods for inducing injury in Prominin-1-expressing cells or methods for suppressing growth of these cells by contacting Prominin-1-expressing cells with an anti-Prominin-1 antibody. The anti-Prominin-1 antibody has been described above. Cells to which the anti-Prominin-1 antibodies bind are not particularly limited as long as they are Prominin-1-expressing cells. Prominin-1-expressing cells of the present invention are preferably cancer cells, and more preferably cancer stem cells.

In the present invention, "contacting" may be carried out in vitro or in vivo. For example, it is carried out by adding an antibody to a culture solution of Prominin-1-expressing cells cultured in a test tube.

Furthermore, in another embodiment, "contacting" in the present invention is carried out by administering to a non-human animal to which Prominin-1-expressing cells have been transplanted into the body, or to an animal carrying cancer cells endogenously expressing Prominin-1. The method of administration may be oral or parenteral administration. The method of administration is particularly preferably parenteral administration, and specifically, the method of administration is, for example, administration by injection, transnasal administration, transpulmonary administration, or transdermal administration. Examples of administration by injection include systemic and local administrations of pharmaceutical compositions, cell proliferation inhibitors, and anticancer agents of the present invention by intravenous injection, intramuscular injection, intraperitoneal injection, subcutaneous injection, or such. A suitable administration method may be selected according to the age of the test animal and symptoms. When administering as an aqueous solution, the aqueous solution may contain only the antibody, or the solution may include, for example, the above-mentioned surfactants, excipients, coloring agents, flavoring agents, preservatives, stabilizers, buffers, suspending agents, isotonic agents, binders, disintegrants, lubricants, fluidity promoting agents, or corrigents. The dosage may be selected from, for example, within the range of 0.0001 mg to 1,000 mg per kg body weight in each administration. Alternatively, for example, the dosage for each patient may be selected from within the range of 0.001 to 100,000 mg/body. However, the dosage of an antibody of the present invention is not limited to these doses.

All prior art references cited herein are incorporated by reference into this description.

EXAMPLES

Herein below, the present invention will be specifically described with reference to the Examples, but it is not to be construed as being limited thereto.

Example 1

Cloning of the Antibody Variable Region and Production of Recombinant Antibody-Expressing Cell Lines Mouse hybridoma cell (HB-12346) expressing the AC133.1 antibody was obtained from ATCC. Hybridoma cells were cultured in a DMEM medium containing 10% fetal bovine serum (FBS), and the cells were harvested. Total RNA was purified from approximately $3\times10^6$ cells using RNeasy Mini (QIAGEN). A 5' RACE cDNA library was prepared from 1 μg of purified total RNA using the SMART RACE cDNA Amplification Kit (Clontech) according to the instructions in the attached manual. The antibody heavy chain variable region (VH) (nucleotide sequence, SEQ ID NO: 9; amino acid sequence, SEQ ID NO: 10) and the light chain variable region (VL) (nucleotide sequence, SEQ ID NO: 17; amino acid sequence, SEQ ID NO: 18) were amplified by PCR using a combination of primers that anneal to portions of the antibody constant region and the Universal Primer Mix included in the SMART RACE cDNA Amplification Kit.

Heavy Chain (IgG1) Amplification Primer:

```
5'-CCATGGAGTTAGTTTGGGCAGCAGATCC-   (SEQ ID NO: 25)
3'
```

Light Chain (Igκ) Amplification Primer:

```
5'-GGCACCTCCAGATGTTAACTGCTCACT-3'  (SEQ ID NO: 26)
```

The reaction solution was prepared according to the manufacturer's instructions using Advantage 2 DNA polymerase of the RACE Kit. A denaturation reaction at 94° C. for 30 seconds was followed by 30 cycles of amplification reaction at 94° C. for 10 seconds, 68° C. for 30 seconds, and 72° C. for 60 seconds. After confirming the amplification of DNA fragments of the predicted size by agarose gel electrophoresis, the amplified fragments were excised and purified. The purified amplified fragments were incorporated into the pGEM-T Easy Vector, and *E. coli* DH5α was transformed by this recombinant plasmid. Plasmid clones that have incorporated amplified fragments of the antibody variable region were selected and their nucleotide sequences were determined.

VH and VL were amplified by PCR using the T7 primer and a primer designed to anneal to the 3'-side variable region, and inserted into an animal cell expression vector having a mouse IgG2a heavy chain constant region and an animal cell expression vector having an Igκ light chain constant region, so that the antibody translation sequence is ligated in frame. The antibody gene is designed to be transcribed under the mouse CMV promoter in these animal cell expression vectors. The heavy chain antibody nucleotide sequence in the constructed expression vector and its translated sequence are shown in SEQ ID NO: 1 and SEQ ID NO: 2, respectively. The mouse Igκ light chain nucleotide sequence and its translated sequence are shown in SEQ ID NO: 3 and SEQ ID NO: 4, respectively. After linearizing the heavy- and light-chain antibody expression vectors by PvuI digestion, DG44 cells (Invitrogen) were transformed by electroporation. Recombinant cell clones were selected using geneticin resistance and nucleic acid non-auxotrophy as indicators, which were conferred by selection markers on the heavy- and light-chain expression vectors. The amount of antibody in the culture supernatant of the cloned recombinant cells was determined by the sandwich ELISA method using anti-mouse antibodies, and cells highly expressing the recombinant antibody were selected. The selected recombinant cells were cultured in the CHO-S-SFMII medium (Invitrogen), and the recombinant mouse IgG2a antibody was purified from the culture supernatant using a HiTrap Protein G Column (Amersham Bioscience) according to the attached manual. AC133.1 antibody (subtype IgG1) was purified as a positive control from the hybridoma culture supernatant using a HiTrap Protein G Column.

Example 2

Confirmation of the Binding Activity of the Recombinant Antibodies and Evaluation of Cytotoxic Activity Flow cytometry was used to confirm that the recombinant antibody produced by cloning the antibody variable regions have the same binding characteristics as the hybridoma-produced antibody. The AC133.1 antibody has been reported to bind to the human retinoblastoma cell line WERI-Rb-1 (Yin et al., Blood (1997) 90: 5002-12). WERI-Rb-1 cells (HTB-169) were obtained from ATCC. WERI-Rb-1 cells were cultured using RPMI1640 medium containing 10% fetal bovine serum at 37° C. under 5% $CO_2$. The cell culture was centrifuged, the supernatant was removed and the cells were suspended in FACS buffer (phosphate buffer containing 2% fetal bovine serum). The recombinant antibody, hybridoma antibody, and mouse IgG antibody which serves as negative control were individually added at a final concentration of 5 μg/mL, and incubated at 4° C. for 30 minutes. After centrifugation, removal of supernatant, and resuspension in FACS buffer, it was centrifuged again. The precipitated cells were suspended in FITC-labeled goat $F(ab')_2$ anti-mouse IgG (H+L) antibody solution (Beckman-Coulter, IM0819) diluted 150-fold with FACS buffer, and then incubated in the dark at 4° C. for 30 minutes. After centrifugation, the cells were suspended in FACS buffer, and binding of the antibodies to the cells was analyzed by FACS Calibur (BD). The recombinant antibody was confirmed to bind to WERI-Rb-1 cells in the same manner as the hybridoma-produced antibody (FIG. 1).

Complement-dependent cytotoxicity (CDC) activities and antibody-dependent cellular cytotoxicity (ADCC) activities of the hybridoma-produced antibody and recombinant IgG2a antibody against WERI-Tb-1 cells were investigated by the chromium release assay. Chromium-51 (Amersham Bioscience, CJS4) was added to the WERI-Rb-1 cell culture medium and incubation was continued for a few hours. After washing the cells with the medium, the radiolabeled cells were spread onto a 96-well culture plate. Then, antibodies were added to a final concentration of 1 μg/mL. For evaluation of the CDC activity, baby rabbit complement was further added to a final concentration of 5%, and the plate was left to stand in a 5% $CO_2$ incubator at 37° C. for 1.5 hours. For evaluation of the ADCC activity, effector cells were added to each well at excess relative to the amount of the target WERI-Rb-1 cells, and the plate was left to stand in a 5% $CO_2$ incubator at 37° C. for six hours. Cells obtained by culturing the spleen cells of a C3H/HeNCrlCrlj mouse (Charles River Japan) in a medium containing human interleukin 2 (Peprotech, 200-02) (50-fold with respect to the target cell), or bone marrow cells cultured in a medium containing human interleukin 2 and mouse GM-CSF (Peprotech, 315-03) (25 fold relative to the target cells) were added and used as effector cells. After static culture, the plates were centrifuged, and a fixed amount of the supernatant was collected from each well, and radioactivity was measured using a gamma counter Wallac 1480. The specific chromium release rate (%) was determined by the following equation.

$$\text{Specific chromium release rate (\%)}=(A-C)/(B-C)\times 100$$

Herein, A represents the radioactivity in each well, B represents the mean value of radioactivity released into the medium upon cell lysis by Nonidet P-40 at a final concentration of 1%, and C represents the mean value of radioactivity when only medium is added.

Figure 2:
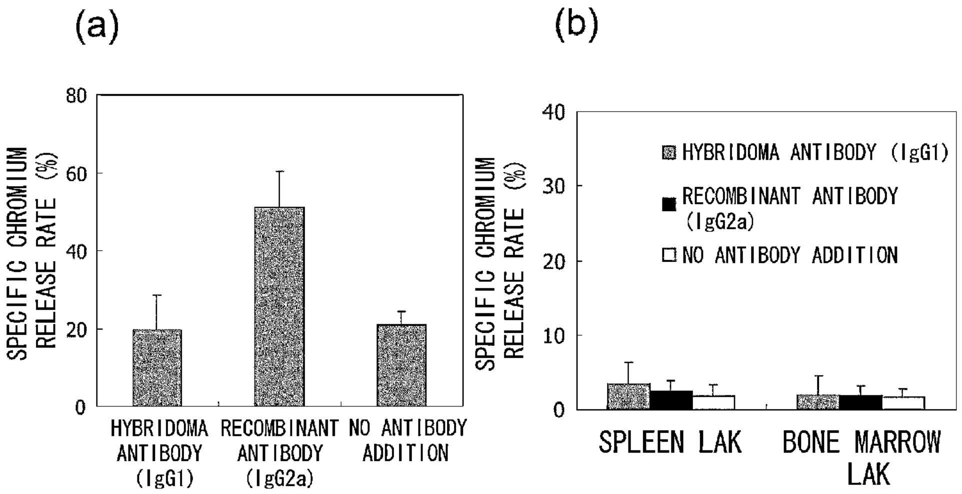
FIG. 2 shows the induction of cytotoxicity by hybridoma-produced and recombinant antibodies; (a) CDC activity and (b) ADCC activity. The recombinant IgG2a antibody has CDC activity. The ability to induce ADCC was not observed in mouse IgG1 and IgG2a antibodies.

Duplicate measurements were taken for each experimental condition, and the mean value was calculated (FIG. 2). While CDC activity was not observed in the IgG1-type AC133 antibody produced by hybridomas, induction of the CDC activity was observed with the recombinant IgG2a antibody. ADCC activity was not observed in either of the hybridoma antibody and recombinant antibody.

Example 3

Preparation of Human Chimeric Antibody and Evaluation of ADCC Activity

The heavy chain variable region sequence was amplified by PCR using the primers shown below, and after EcoRI/NheI digestion, it was incorporated into the heavy chain cloning site in a human chimeric antibody expression vector. The light chain variable region sequence was amplified by PCR using the primer set shown below in a similar manner, and after BamHI/BsiWI digestion, it was incorporated into the light chain cloning site in the above-mentioned human chimeric antibody expression vector into which the heavy chain sequence has been introduced. In the cell expression vectors constructed, both the heavy chain and light chain antibody genes are designed so that the genes are transcribed under the control of a mouse CMV promoter.

```
VH chimeric primer 1:
5'-CTTGAATTCCACCATGGAATGGAGCTGGGTCTTTC-3'

VH chimeric primer 2:
5'-CGCGCTAGCTGCAGAGACAGTGACCAGAGTCC-3'

VL chimeric primer 1:
5'-CAGGGATCCACCATGAATTTGCCTGTTCATCTCTT-3'

VL chimeric primer 2:
5'-CGGCGTACGTTTTATTTCCAGCTTGGTCCC-3'
```

A nucleotide sequence of the human chimeric antibody heavy chain is shown in SEQ ID NO: 5 and its translated sequence is shown in SEQ ID NO: 6. A nucleotide sequence of the human chimeric antibody light chain is shown in SEQ ID NO: 7 and its translated sequence is shown in SEQ ID NO: 8.

YB2/0 (ATCC) was transformed by the electroporation method using a human chimeric antibody expression vector. Recombinant cell clones were selected using as an indicator geneticin resistance, which was conferred by a selection marker on the human chimeric antibody expression vector. The amount of antibody in the cell culture supernatant of the cloned recombinant cells was detected by the sandwich ELISA method using anti-human antibodies, and recombinant antibody-expressing cells were selected. The selected recombinant cells were cultured in an RPMI1640 medium containing 10% Ultra-Low IgG fetal bovine serum (Invitrogen), and the human chimeric antibody was purified from the culture supernatant of these cells using a HiTrap Protein A Column (Amersham Bioscience) according to the attached manual.

Figure 3:
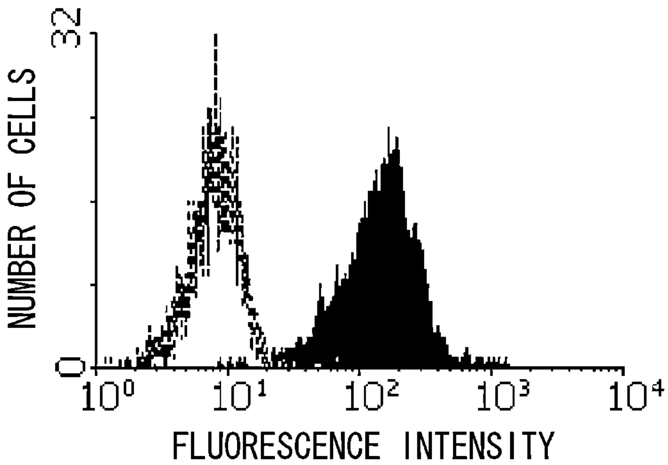
FIG. 3 shows binding of the human chimeric antibody to WERI-Rb-1 cells. The dotted-line histogram shows the staining results obtained with the negative control human IgG antibody. The black-filled histogram shows the staining results obtained with the recombinant chimeric antibody.

Flow cytometry was used to analyze the binding of the purified human chimeric antibody to WERI-Rb-1 cells. The human chimeric antibody and human polyclonal IgG antibody which serves as negative control were individually added to react a suspension solution of WERI-Rb-1 cells at a final concentration of 5 μg/mL. The cell-bound antibodies were labeled with FITC-labeled goat $F(ab')_2$ anti-human IgG (H+L) antibody (Beckman-Coulter, IM0839), and then analyzed by FACS Calibur. Binding of the human chimeric antibody to the cells was confirmed (FIG. 3).

Figure 4:
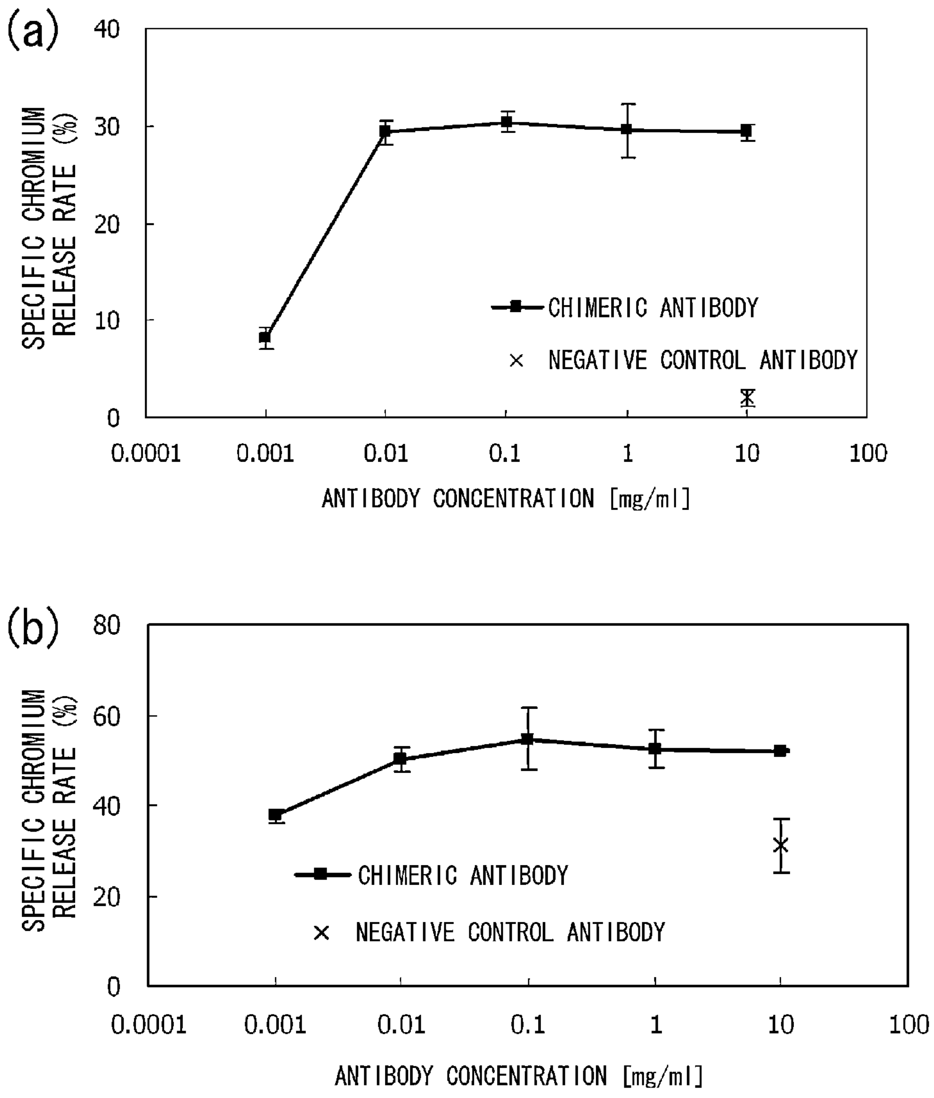
FIG. 4 shows the induction of ADCC activity by the human chimeric antibody in (a) WERI-Rb-1 cells and (b) HuH7 cells.

ADCC activities of the human chimeric antibody against WERI-Rb-1 and the human liver cancer cell line HuH7 were investigated by the chromium release assay. Huh7 cells were spread and attached to a 96-well plate, then Chromium-51 was added, and the cells were cultured for a few hours. Culture medium was removed, the cells were washed with medium, and then fresh medium was added. Chromium-51 was added to the WERI-Rb-1 cell culture medium, and incubation was continued for a few hours. After washing the cells with medium, the radiolabeled cells were spread onto a 96-well culture plate. Then, the antibody was added, and to each well, effector cells (a recombinant cell produced by forced expression of the human Fc-gamma receptor 3 (NM_000569) in NK-92 (ATCC, CRL-2407)) were added so that the amount of effector cells added was approximately five times that of the target cells, and the plate was left to stand in a 5% $CO_2$ incubator at 37° C. for four hours. After static culture, the plate was centrifuged, and a fixed amount of the supernatant was collected from each well, and radioactivity was measured using a gamma counter Wallac 1480 to determine the specific chromium release rate (%). As shown in FIG. 4, the human chimeric antibody induced ADCC activity against WERI-Rb-1 and HuH7 cells in a manner dependent of the antibody dose.

Example 4

Production of Cell Lines Forcedly Expressing Human Prominin-1

Prominin-1 (NM_006017) is the antigen molecule of AC133.1. DNA fragments comprising the Prominin-1 translation sequence were amplified by the PCR method from the human kidney cDNA library as template, and cloned into animal cell expression vectors. The expression vectors were introduced into DG44 cells by electroporation, and recombinant cells were selected using geneticin. Expression of the Prominin-1 recombinant protein in the recombinant cells was confirmed by Western blotting with an anti-FLAG M2 antibody, using the FLAG-tag artificially added to the C terminus of the recombinant protein. Specific binding of the A133.1 antibody to cells forcedly expressing Prominin-1 was confirmed by flow cytometry.

Example 5

Design of the Humanized Antibody Sequence and Preparation of the Humanized Antibody To reduce immunogenicity when antibodies are administered to humans, CDRs of the AC133.1 antibody were grafted into the human antibody sequence to produce humanized antibodies. BLAST sequence homology search (program TBLASTN 2. 2. 12) to the GenBank nucleotide sequence database was performed using the AC133.1 antibody variable region framework amino acid sequence as a query. Of the highly homologous human antibody sequences identified as hits from the search, AF174028 (H chain) and AB064105 (L chain) were selected as antibody sequences for use in CDR grafting. Sequence alignment of the AC133 antibody variable region framework sequences and the human antibody sequences selected as templates for CDR-grafting are shown in FIG. 5. The nucleotide sequence and amino acid sequence of the CDR-grafted humanized antibody H chain sequence (h133H) are shown in SEQ ID NO: 31 and SEQ ID NO: 32, respectively; and the nucleotide sequence and amino acid sequence of the CDR-grafted humanized antibody L chain sequence (h133L) are shown in SEQ ID NO: 33 and SEQ ID NO: 34, respectively.

The humanized L chain variable region sequence was synthesized by the following method. Oligonucleotides HuKf1 and HuKr1, HuKf2 and HuKr2, HuKf3 and HuKr3, and HuKf4 and HuKr4 shown in Table 1 were mixed into the KOD DNA polymerase (TOYOBO) reaction solution to a final concentration of 10 nM. Double-strand elongation of the oligonucleotides was carried out by reaction at 94° C. for 2 minutes, and 25 cycles of 98° C. for 10 seconds, 57° C. for 30 seconds, and 68° C. for 1 minute. 1 μL each of the above-mentioned double-strand elongation solutions, and primers hu133VKfSal and hu133VKrBsi shown in Table 2 were mixed into a KOD DNA polymerase reaction solution, and a fragment-assembly reaction (94° C. for 2 minutes, followed by 25 cycles of 98° C. for 10 seconds, 57° C. for 30 seconds, and 68° C. for 1 minute) was carried out. After addition of A to the ends of the assembled DNA fragments using ExTaq DNA polymerase, agarose electrophoresis was performed. A band of the desired size was excised, and cloned into the pGEM-T Easy Vector (Promega), and then DNA sequence analysis was performed to select plasmids carrying the correct sequence. The L chain variable region sequence fragment was excised from the selected plasmid by SalI/BsiWI restriction enzyme digestion, and incorporated into an animal cell expression vector for antibody under transcriptional control of the mouse CMV promoter so that it will be translated correctly as human Igκ antibody.

TABLE 1

| Template oligonucleotides used to produce the humanized antibody variable region sequence |
|---|
| huHf1 (SEQ ID NO: 55);<br>gcgaattcaccatggactggacctggagcatccttttcttggtggcagca<br>gcaacaggtgcccactcccaggttcagctg |

TABLE 1-continued

| Template oligonucleotides used to produce the humanized antibody variable region sequence |
|---|
| huHf2 (SEQ ID NO:5 6);<br>gaagaagcctggggcctcagtgaaggtctcctgcaaggcttctggttaca<br>cctttaccGACTTTGAAATGCACtgggtgc |
| huHf3 (SEQ ID NO: 57);<br>cttgagtggatgggaGATATTGATCCTGGAACTGGTGATACTGCCTACAA<br>TCTGAAGTTCAAGGGCagagtcaccatgac |
| huHf4 (SEQ ID NO: 58);<br>agcctacatggagctgaggagcctgagatctgacgacacggccgtgtatt<br>actgtgcgttgGGGGCCTTTGTTTACtgg |
| huHr1 (SEQ ID NO: 59);<br>gagaccttcactgaggccccaggcttcttcacctcagctccagactgcac<br>cagctgaacctgggagtgggcacctgttgc |
| huHr2 (SEQ ID NO: 60);<br>TCCAGGATCAATATCtcccatccactcaagcccttgtccaggggcctgtc<br>gcacccaGTGCATTTCAAAGTCggtaaagg |
| huHr3 (SEQ ID NO: 61);<br>atctcaggctcctcagctccatgtaggctgtgctcgtggatgtgtctgtg<br>gtcatggtgactctGCCCTTGAACTTCAGA |
| huHr4 (SEQ ID NO: 62);<br>gcgctagctgaggagacggtgaccagggttccctggccccaggggtcgaa<br>ccaGTAAACAAAGGCCCCcaacgcacagta |
| huKf1 (SEQ ID NO: 63);<br>gctgtcgaccaccatgaaatacctattgcctacggcagccgctggattgt<br>tattactcgcggcccagccggccatggccg |
| huKf2 (SEQ ID NO: 64);<br>ccactctccctgcccgtcacccctggagagccggcctccatctcctgcAG<br>GTCTAGTCAGAGTCTTGCAAACAGTTATGG |
| huKf3 (SEQ ID NO: 65);<br>acctgcagaagccagggcagtctccacagctcctgatctatGGGATTTCC<br>AACAGATTTTCTggggtccctgacaggttc |
| huKf4 (SEQ ID NO: 66);<br>agattttacactgaaaatcagcagagtggaggctgaggatgttggggttt<br>attactgcTTACAAGGTACACATCAGCCGT |
| huKr1 (SEQ ID NO: 67);<br>ctctccaggggtgacgggcagggagagtggagactgagtcatcacaacat<br>cggccatggccggctgggccgcgagtaata |
| huKr2 (SEQ ID NO: 68);<br>gctgtggagactgccctggcttctgcaggtaccaAGACAAATAGGTGTTC<br>CCATAACTGTTTGCAAGACTCTGACTAGAC |
| huKr3 (SEQ ID NO: 69);<br>tccactctgctgattttcagtgtaaaatctgtgcctgatccactgccact<br>gaacctgtcagggaccccAGAAAATCTGTT |
| huKr4 (SEQ ID NO: 70);<br>cggcgtacgtttgatctccagcttggtcccctggccaaaCGTGTACGGCT<br>GATGTGTACCTTGTAAgcagtaat |

TABLE 2

| PCR primers used to produce the humanized antibody variable region sequence and their derivatives |
|---|
| hu133VHfEco (SEQ ID NO: 71);<br>GCGAATTCACCATGGACTGGACCTGGAGCA |
| hu133VHrNhe (SEQ ID NO: 72);<br>CGCGCTAGCTGAGGAGACGGTGACCAGGGT |
| hu133VKfSal (SEQ ID NO: 73);<br>GCTGTCGACCACCATGAAATACCTATTGCC |

TABLE 2-continued

| PCR primers used to produce the humanized antibody variable region sequence and their derivatives |
|---|
| hu133VKrBsi (SEQ ID NO: 74);<br>CGGCGTACGTTTGATCTCCAGCTTGGTCCC |
| FR4delta_f (SEQ ID NO: 75);<br>GGGGCCTTTGTTTACTGGGGCCAGGGAACC |
| FR4delta_r (SEQ ID NO: 76);<br>GGTTCCCTGGCCCCAGTAAACAAGGCCCC |
| MCMV-F1 (SEQ ID NO: 77);<br>TAACACCGCCCCGGTTTTCC |
| G1kCH-r3 (SEQ ID NO: 78);<br>AGTAGAGTCCTGAGGACTGTAGG |
| G1kCL-r1 (SEQ ID NO: 79);<br>TCTAGGTGCTGTCCTTGCTGTCC |
| AC133CDR1f (SEQ ID NO: 80);<br>TAGTCAGAGTCTTGCAAACAGTTATGGGAA |
| AC133CDR1r (SEQ ID NO: 81);<br>CAAATAGGTGTTCCCATAACTGTTTGCAAG |
| M4V_f (SEQ ID NO: 82);<br>atggccgatgttgtgGtgactcagtctcca |
| M4V_r (SEQ ID NO: 83);<br>tggagactgagtcaCcacaacatcggccat |
| P15Ff (SEQ ID NO: 84);<br>ctgcccgtcaccTTtggagagccggcctcc |
| P15Fr (SEQ ID NO: 85);<br>ggaggccggctctccaAAggtgacgggcag |
| P18Qf (SEQ ID NO: 86);<br>cacccctggagagcAAgcctccatctcctg |
| P18Qr (SEQ ID NO: 87);<br>caggagatggaggcTTgctctccaggggtg |
| PPFQf (SEQ ID NO: 88);<br>ccgtcaccTTtggagagcAAgcctccatct |
| PPFQr (SEQ ID NO: 89);<br>agatggaggcTTgctctccaAAggtgacgg |
| A19V_f(SEQ ID NO: 90);<br>TGGAGAGCCGGTCTCCATCTCCTGCAGGTC |
| A19V_r (SEQ ID NO: 91);<br>GACCTGCAGGAGATGGAGACCGGCTCTCCA |
| PAQV_f(SEQ ID NO: 92);<br>TGGAGAGCAAGTCTCCATCTCCTGCAGGTC |
| PAQV_r (SEQ ID NO: 93);<br>GACCTGCAGGAGATGGAGACTTGCTCTCCA |

The humanized H chain variable region sequence was synthesized by a method similar to that for the L chain. 1 μL each of the double-strand elongation solutions of the oligonucleotides HuHf1 and HuHr1, HuHf2 and HuHr2, HuHf3 and HuHr3, and HuHf4 and HuHr4 shown in Table 1, and primers hu133VHfEco and hu133VHrNhe shown in Table 2 were mixed into a KOD DNA polymerase reaction solution, and a PCR-assembly reaction was carried out. After cloning the PCR-amplified fragment into a vector, nucleotide sequence analysis was performed, and plasmids were selected. The H chain variable region sequence fragment was excised by EcoRI/NheI restriction enzyme digestion, and incorporated into an animal cell expression vector for human IgG1 antibody under transcriptional control of the mouse CMV promoter. There was a sequence inserted in the completed H chain variable region sequence as a result of an error in the design of the template oligonucleotides. Therefore, using this as template, PCR amplification was conducted with FR4delta_f and the G1kCH-r3 primer which is complementary to a sequence on the vector, and FR4delta_r and the MCMV-F1 primer which is complementary to a sequence on the vector. These two fragments were reassembled to prepare a sequence fragment encoding the initially planned antibody variable region. This was incorporated into a human IgG1 antibody expression vector, and the construct was confirmed by nucleotide sequence analysis.

After linearizing the humanized antibody expression vector by PvuI digestion, DG44 cells (Invitrogen) were transformed by electroporation. Recombinant cell clones were selected using as an indicator geneticin resistance conferred by a selection marker on the expression vector. The amount of antibody in the culture supernatant of the cloned recombinant cells was detected by the sandwich ELISA method using anti-human antibodies, and cells highly expressing the recombinant antibody were selected. The selected recombinant cells were cultured using the CHO-S-SFMII medium (Invitrogen), and the humanized antibody was purified from the culture supernatant using a HiTrap Protein A Column (Amersham Bioscience) according to the attached manual. As positive control, the chimeric antibody was purified by the same method from the culture supernatant of chimeric antibody-expressing DG44 cells established by the same method using a HiTrap Protein A Column.

Figure 6:
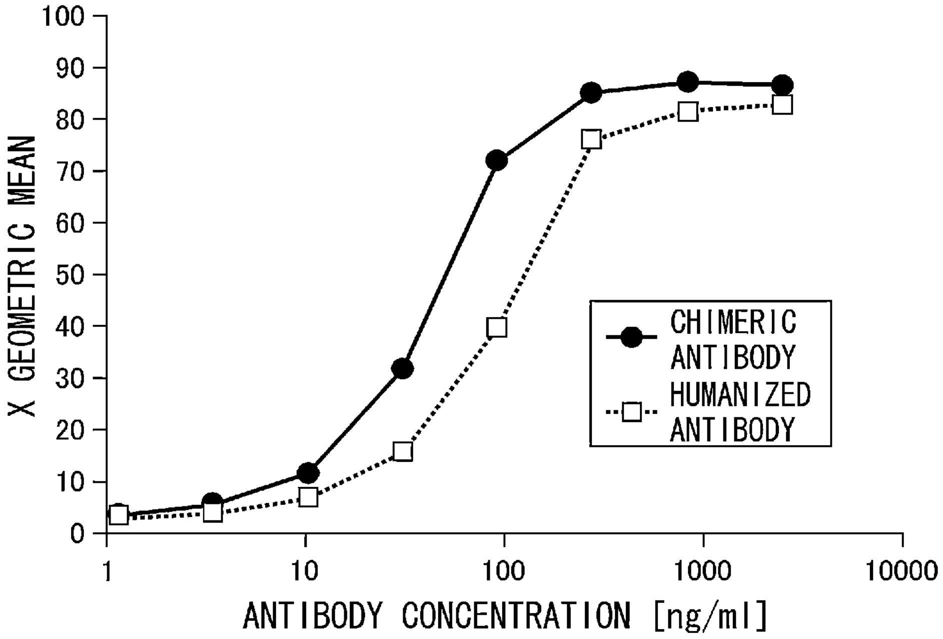
FIG. 6 shows the binding ability of the humanized antibody comprising h133H/h133La to the antigen-expressing WERI-Rb-1 cells. The h133H/h133La-comprising humanized antibody binds to WERI-Rb-1 cells in a dose-dependent manner.

Flow cytometry was used to analyze the antigen-binding activity of the humanized antibody. Serially diluted humanized antibody and chimeric antibody were mixed with WERI-Rb-1, and then incubated at 4° C. for 30 minutes. After centrifugation, removal of supernatant, and then resuspension in FACS buffer, it was centrifuged again. The precipitated cells were suspended in FITC-labeled goat $F(ab')_2$ anti-human IgG (H+L) antibody solution (Beckman-Coulter) diluted 150-fold with FACS buffer, and then incubated in the dark at 4° C. for 30 minutes. After centrifugation, the cells were suspended in FACS buffer, the amount of antibody bound per cell was measured by FACS Calibur, and X geometric mean of the cell fluorescence intensity was calculated using the attached analysis software, CELLQuest Pro. As summarized in FIG. 6, the humanized antibody comprising the humanized antibody H chain sequence (h133H) (nucleotide sequence, SEQ ID NO: 31; amino acid sequence, SEQ ID NO: 32) and the humanized antibody L chain sequence (h133L) (nucleotide sequence, SEQ ID NO: 33; amino acid sequence, SEQ ID NO: 34) bound to the antigen-expressing WERI-Rb-1 cells in a dose-dependent manner. However, the humanized antibody had a lower affinity to the antigen than the chimeric antibody having the original AC133 mouse variable region sequences.

Example 6

Enhancement of Binding Activity of the Humanized Antibody by Introducing Amino Acid Residue Substitutions The reason that the humanized antibody has a lower binding affinity to the antigen than the mouse antibody is because amino acid residues that should have been conserved to maintain binding activity were replaced in the process of humanization. To map to see whether the amino acid residue to be conserved exists on the H chain or L chain, the combination of H chains and L chains in the chimeric and humanized antibodies were exchanged, and these antibodies were evaluated to see whether the antigen-binding activity is conserved. Antibodies were transiently expressed in COS-7 cells using the following combinations, and their binding activities were evaluated.

(1) chimeric H chain (SEQ ID NO: 6) and chimeric L chain (SEQ ID NO: 8)

(2) chimeric H chain (SEQ ID NO: 6) and humanized L chain (SEQ ID NO: 34)

(3) humanized H chain (SEQ ID NO: 32) and chimeric L chain (SEQ ID NO: 8)

(4) humanized H chain (SEQ ID NO: 32) and humanized L chain (SEQ ID NO: 34)

Figure 7:
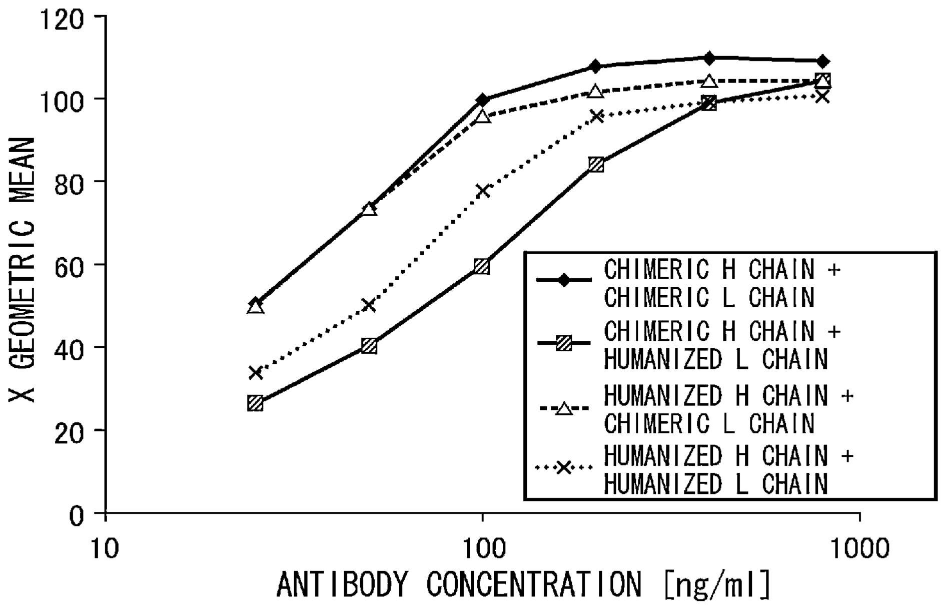
FIG. 7 shows the results of comparing the binding activities of antibodies from combinations of H chains and L chains. The antibodies comprised of the humanized L chain have a reduced binding activity.

COS-7 was seeded into a 6-well plate at $2\times10^5$ cells/well, and cultured overnight. Each of the antibody expression vector combinations was introduced into COS-7 cells using the DNA transfection reagent FuGENE-6 (Roche Diagnostics) according to the manufacturer's manual. After three days of culture, the culture supernatants were collected. The antibody concentration in the collected supernatants was determined by sandwich ELISA using anti-human antibodies. Using the method described in Example 5, antigen binding was analyzed by flow cytometry and the results are summarized in FIG. 7. As a result, an antibody in the combination of a humanized H chain and a chimeric L chain show equivalent binding activity to both the chimeric H chain and L chain antibody, whereas in combinations that use the humanized L chain, that is, the combination of chimeric H chain and humanized L chain and the combination of humanized H chain and humanized L chain, decreased binding activity was observed. These results indicate that for maximum conservation of antigen-binding activity, it is necessary to substitute any of the amino acid residues on the humanized L chain sequence with the corresponding amino acid residues of the mouse sequence. Then, to elucidate the location of the site to be substituted on the humanized L chain variable sequence, an L chain of the mouse-human hybrid variable region sequence, such as those indicated in FIG. 8 (B) was produced. More specifically, hybrid L1 is a humanized antibody sequence (nucleotide sequence, SEQ ID NO: 35; amino acid sequence, SEQ ID NO: 36) carrying the FR1 mouse sequence (the signal sequence is also derived from the mouse antibody sequence), and hybrid L2 is a chimeric antibody sequence (nucleotide sequence, SEQ ID NO: 37; amino acid sequence, SEQ ID NO: 38) carrying the FR1 humanized sequence (the signal sequence is also derived from the humanized antibody sequence).

Methods for producing hybrid L1 and hybrid L2 variable region sequences are described below.

A 5'-side fragment of the hybrid L1 variable region was amplified using the chimeric antibody L chain expression vector as template, with the MCMV-F1 and AC133CDR1r primer combination. The hybrid L1 3'-side fragment was amplified using the humanized antibody L chain expression vector as template, with the G1kCLr1 and AC133CDR1f primer combination. Reaction was carried out using KOD DNA polymerase according to the manufacturer's instructions. Agarose electrophoresis was performed to isolate fragments of the desired size, and after purification, two fragments were combined for PCR amplification using the MCMV-F1 and G1kCLr1 primers. After the amplification, the assembled fragment was excised, and after SalI/BsiWI digestion, this was incorporated into the L chain expression vector. Similarly, for the hybrid L2 variable region, the 5'-side fragment of the hybrid L2 variable region was amplified by PCR using the humanized antibody L chain expression vector as template, with the MCMV-F1 and AC133CDR1r primer combination; and the 3'-side fragment was amplified by PCR using the chimeric antibody L chain expression vector as template, with the G1kCLr1 and AC133CDR1f primer combination, and these were then assembled and cloned into an expression vector. Nucleotide sequence analysis confirmed that the constructed expression vector had the expected sequence.

Figure 9:
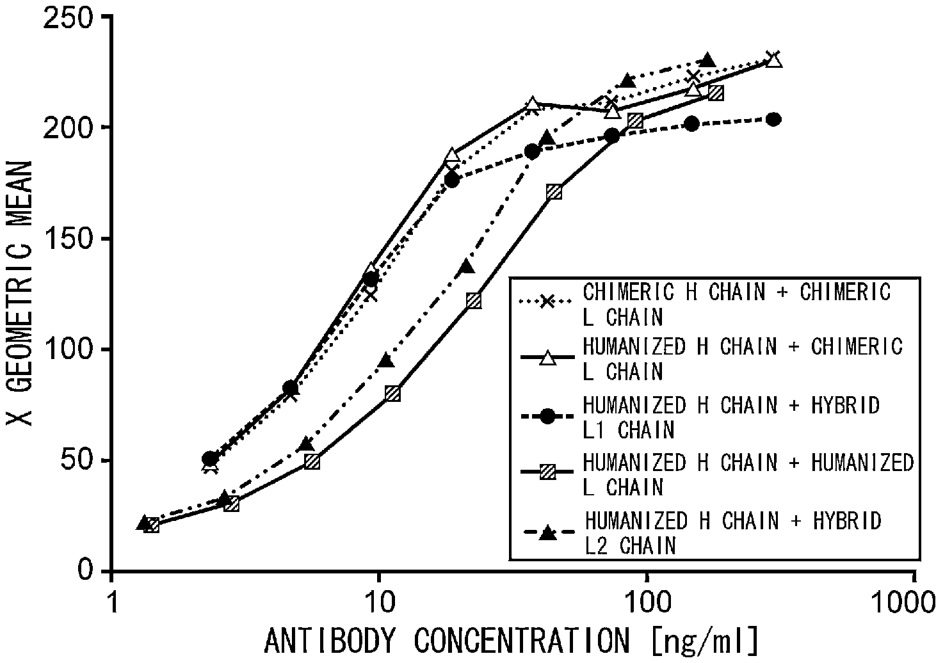
FIG. 9 shows the result of comparing the binding activity after superimposing the hybrid L1 chain and the hybrid L2 chain antibodies to the combinations of FIG. 7. The antigen binding activity of the hybrid L1 chain antibody is equivalent to that of the chimeric L chain.

The following were added to the aforementioned combination to transiently express the antibody in COS-7 cells, and the binding activity was evaluated by flow cytometry (FIG. 9).

(5) humanized H chain and hybrid L1

(6) humanized H chain and hybrid L2

As a result, the hybrid L1 chain was found to have equivalent activity to the chimeric L chain. According to the above-mentioned results, a key amino acid residue may exist on humanized L chain framework 1. So, modified antibodies were prepared by introducing mutations into the sites on L chain frame work 1 shown in FIG. 8 (B) that had underwent humanization-associated amino acid residue substitutions and effects on binding activity were examined.

Methods for producing the humanized L-chain-modified antibodies are as follows.

Construction of the h133L (b) chain (nucleotide sequence, SEQ ID NO: 39; amino acid sequence, SEQ ID NO: 40). Using the humanized antibody L chain expression vector as a template, PCR amplification was carried out using the MCMV-F1 and M4V_r primer combination for the 5'-side fragment and the G1kCLr1 and M4V_f primer combination for the 3'-side fragment, the fragments were then assembled. After SalI/BsiWI restriction enzyme digestion, the resulting fragment was cloned into an expression vector.

Construction of the h133L (c) chain (nucleotide sequence, SEQ ID NO: 41; amino acid sequence, SEQ ID NO: 42). Using the humanized antibody L chain expression vector as a template, PCR amplification was carried out using the MCMV-F1 and P15Fr primer combination for the 5'-side fragment and the G1kCLr1 and P15Ff primer combination for the 3'-side fragment, the fragments were then assembled. After SalI/BsiWI restriction enzyme digestion, the fragment was cloned into an expression vector.

Construction of the h133L (d) chain (nucleotide sequence, SEQ ID NO: 43; amino acid sequence, SEQ ID NO: 44). Using the humanized antibody L chain expression vector as a template, PCR amplification was carried out using the MCMV-F1 and P18Qr primer combination for the 5'-side fragment and the G1kCLr1 and P18Qf primer combination for the 3'-side fragment, the fragments were then assembled. After digestion with SalI/BsiWI restriction enzyme, the fragment was cloned into an expression vector.

Construction of the h133L (e) chain (nucleotide sequence, SEQ ID NO: 45; amino acid sequence, SEQ ID NO: 46). Using the humanized antibody L chain expression vector as a template, PCR amplification was carried out using the MCMV-F1 and PPFQr primer combination for the 5'-side fragment and the G1kCLr1 and PPFQf primer combination for the 3'-side fragment, the fragments were then assembled. After digestion with SalI/BsiWI restriction enzyme, the fragment was cloned into an expression vector.

Construction of the h133L (f) chain (nucleotide sequence, SEQ ID NO: 47; amino acid sequence, SEQ ID NO: 48). Using the humanized antibody L chain expression vector as a template, PCR amplification was carried out using the MCMV-F1 and A19V_r primer combination for the 5'-side fragment and the G1kCLr1 and A19V_f primer combination for the 3'-side fragment, the fragments were then assembled. After digestion with SalI/BsiWI restriction enzyme, the fragment was cloned into an expression vector.

Construction of the h133L (g) chain (nucleotide sequence, SEQ ID NO: 49; amino acid sequence, SEQ ID NO: 50). Using the humanized antibody L (c)-chain expression vector as a template, PCR amplification was carried out using the MCMV-F1 and A19V_r primer combination for the 5'-side fragment and the G1kCLr1 and A19V_f primer combination for the 3'-side fragment, the fragments were then assembled. After digestion with SalI/BsiWI restriction enzyme, the fragment was cloned into an expression vector.

Construction of the h133L (h) chain (nucleotide sequence, SEQ ID NO: 51; amino acid sequence, SEQ ID NO: 52). Using the humanized antibody L (e)-chain expression vector as the template, PCR amplification was carried out using the MCMV-F1 and PAQV_r primer combination for the 5'-side fragment and the G1kCLr1 and PAQV_f primer combination for a 3'-side fragment, the fragments were then assembled. After digestion with SalI/BsiWI restriction enzyme, the fragment was cloned into an expression vector.

Nucleotide sequence analyses confirmed that all of the constructed expression vectors had the expected sequences.

Together with a humanized H chain, humanized L-chain-modified antibodies were transiently expressed in COS-7 cells. Flow cytometry was used to evaluate and compare the binding activity of the combination of a humanized H chain and a humanized L chain, a humanized H chain and a chimeric L chain, and a humanized H chain and a hybrid L1 chain.

Figure 10:
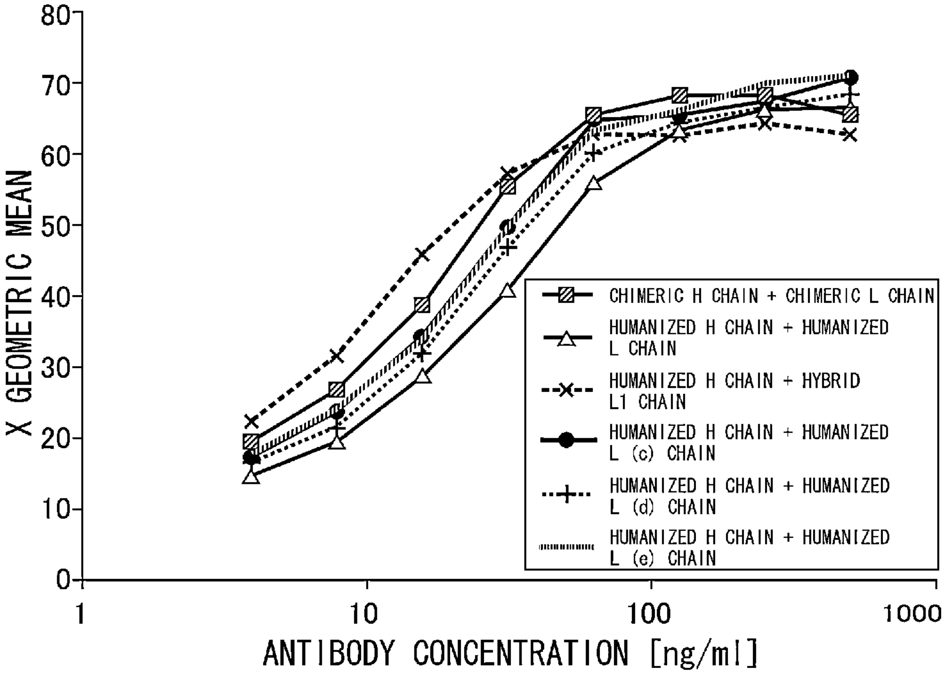
FIG. 10 shows the binding activity of the humanized L-chain-modified antibodies.

The h133L (b) modified antibody did not show a greater activity than the humanized L chain (data not shown). The P15F point-mutated L (c) modified antibody showed elevated binding activity compared to the humanized L chain (FIG. 10). The binding activity of the L (e) modified antibody produced by introducing mutations at two positions, P15F and P18Q, was nearly equivalent to that of L (c).

Figure 11:
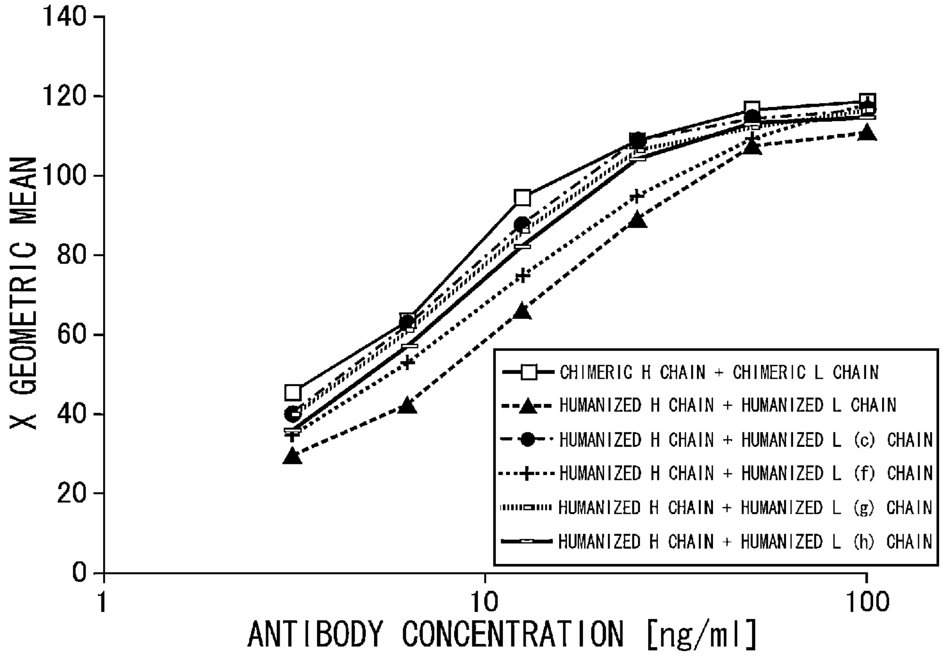
FIG. 11 shows the binding activity of the humanized L-chain-modified antibodies.

Remarkable increase in binding activity was not observed with the L (f) modified antibody (FIG. 11). The modified antibodies L (g) and L (h) produced by introducing additional mutations at one and two positions, respectively, to the L (c) modified antibody did not show greater binding activities greater than L (c).

The combination of humanized H chain with humanized L (c) chain showed nearly equivalent binding activity to the chimeric antibody. From the above-mentioned results, the sequences of the H chain of h133H (nucleotide sequence, SEQ ID NO: 31; amino acid sequence, SEQ ID NO: 32) and the L chain of the h133L (c) chain (nucleotide sequence, SEQ ID NO: 41; amino acid sequence, SEQ ID NO: 42) and combination thereof for the humanized antibodies were determined.

INDUSTRIAL APPLICABILITY

The present invention provides recombinant antibodies with imparted ADCC/CDC-inducing effect that does not exist in the original AC133 antibody. Since the AC133 antibody epitope is expressed in cancer stem cells, antibodies of the present invention can be used as effective anticancer agents to suppress cancer metastasis and promote reduction of primary tumor foci through suppression of tumor growth by targeting cancer stem cells.

Furthermore, while conventional chemotherapeutic agents and antibodies labeled with a cytotoxic substance have problems of side effects in normal cells, antibodies of the present invention specifically suppress cancer stem cells and will be useful as anticancer agents that can reduce side effects in normal cells.

The invention claimed is:

1. A pharmaceutical composition comprising as an active agent an antibody which binds to Prominin-1, wherein the antibody is not bound to a cytotoxic substance, wherein the antibody comprises the amino acid sequence of SEQ ID NO: 12 as a heavy chain variable region CDR1, the amino acid sequence of SEQ ID NO: 14 as a heavy chain variable region CDR2, and the amino acid sequence of SEQ ID NO: 16 as a heavy chain variable region CDR3, and comprises as a light chain variable region the amino acid sequence of position 1 to 112 of SEQ ID NO: 34 wherein the amino acid which corresponds to position 15 in the amino acid sequence of SEQ ID NO: 34 is Phe, and wherein the antibody is a chimeric antibody or humanized antibody comprising a heavy chain constant region of a human IgG1 antibody and a light chain constant region of a human κ chain, and has ADCC activity.

2. The pharmaceutical composition of claim 1, wherein the antibody has CDC activity.

3. The pharmaceutical composition of claim 1, which is an anticancer agent.

4. The pharmaceutical composition of claim 1, wherein the cytotoxic substance is any one of the substances selected from the group consisting of a toxin, a radioactive substance, and a chemotherapeutic agent.

5. A pharmaceutical composition comprising as an active agent an antibody which binds to Prominin-1, wherein the antibody is not bound to a cytotoxic substance, wherein the antibody comprises the amino acid sequence of SEQ ID NO: 12 as a heavy chain variable region CDR1, the amino acid sequence of SEQ ID NO: 14 as a heavy chain variable region CDR2, and the amino acid sequence of SEQ ID NO: 16 as a heavy chain variable region CDR3, and comprises as a light chain variable region the amino acid sequence of position 1 to 112 of SEQ ID NO: 34 wherein the amino acid which corresponds to position 15 in the amino acid sequence of SEQ ID NO: 34 is Phe and wherein the amino acid which corresponds to position 18 in the amino acid sequence of SEQ ID NO: 34 is Gln, and wherein the antibody is a chimeric antibody or humanized antibody comprising a heavy chain constant region of a human IgG1 antibody and a light chain constant region of a human κ chain, and has ADCC activity.

6. The pharmaceutical composition of claim 5, wherein the antibody has CDC activity.

7. The pharmaceutical composition of claim 5, which is an anticancer agent.

8. The pharmaceutical composition of claim 5, wherein the cytotoxic substance is any one of the substances selected from the group consisting of a toxin, a radioactive substance, and a chemotherapeutic agent.

9. A pharmaceutical composition comprising as an active agent an antibody of any one of the isolated antibodies of (a) to (e), wherein the antibody binds specifically to Prominin-1 and is not bound to a cytotoxic substance:

(a) an antibody comprising a heavy chain variable region comprising the amino acid sequence of positions 1 to 114 of SEQ ID NO: 32;

(b) an antibody comprising a light chain variable region comprising the amino acid sequence of positions 1 to 112 of SEQ ID NO: 42;

(c) an antibody comprising a light chain variable region comprising the amino acid sequence of positions 1 to 112 of SEQ ID NO: 46;

(d) an antibody comprising a heavy chain variable region comprising the amino acid sequence of positions 1 to 114 of SEQ ID NO: 32 and a light chain variable region comprising the amino acid sequence of positions 1 to 112 of SEQ ID NO: 42; and (e) an antibody comprising a heavy chain variable region comprising the amino acid sequence of positions 1 to 114 of SEQ ID NO: 32 and a light chain variable region comprising the amino acid sequence of positions 1 to 112 of SEQ ID NO: 46;

wherein the antibody of any one of (a) to (e) is a chimeric antibody or a humanized antibody comprising a heavy chain constant region of human IgG1 and a light chain constant region of a human κ chain, and has ADCC activity.

10. The pharmaceutical composition of claim 9, wherein the antibody has CDC activity.

11. The pharmaceutical composition of claim 9, wherein the cytotoxic substance is selected from the group consisting of a toxin, a radioactive substance, and a chemotherapeutic agent.

12. The pharmaceutical composition of claim 9, which is an anticancer agent.

* * * * *

UNITED STATES PATENT AND TRADEMARK OFFICE

CERTIFICATE OF CORRECTION

PATENT NO. : 8,722,858 B2
APPLICATION NO. : 12/666418
DATED : May 13, 2014
INVENTOR(S) : Kenji Yoshida It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 648 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 93

<210> SEQ ID NO 1
<211> LENGTH: 1392
<212> TYPE: DNA
<213> ORGANISM: Mus musculus

<400> SEQUENCE: 1

```
atggaatgga gctgggtctt tctcttcctc ctgtcagtaa ctgcaggtgt ccaatcccag     60

gttcaactgc agcagtctgg ggctgagctg gtgaggcctg gggcttcagt gaagctgtcc    120

tgcaaggctt cgggctacac attttctgac tttgaaatgc actgggtgaa gcagacacct    180

gtgcatggcc tggaatggat tggagatatt gatcctggaa ctggtgatac tgcctacaat    240

ctgaagttca agggcaaggc cacactgact acagacaaat cttccagcac agcctacatg    300

gagctccgca gcctgacatc tgaggactct gccgtctatt actgtaccct cggggccttt    360

gtttactggg gccaagggac tctggtcact gtctctgcag cgaaaacaac agccccatcg    420

gtctatccac tggcccctgt gtgtggagat acaactggct cctcggtgac tctaggatgc    480

ctggtcaagg gttatttccc tgagccagtg accttgacct ggaactctgg atccctgtcc    540

agtggtgtgc acaccttccc agctgtcctg cagtctgacc tctacaccct cagcagctca    600

gtgactgtaa cctcgagcac ctggcccagc cagtccatca cctgcaatgt ggcccacccg    660

gcaagcagca ccaaggtgga caagaaaatt gagcccagag ggcccacaat caagccctgt    720

cctccatgca aatgcccagc acctaacctc ttgggtggac catccgtctt catcttccct    780

ccaaagatca aggatgtact catgatctcc ctgagcccca tagtcacatg tgtggtggtg    840

gatgtgagcg aggatgaccc agatgtccag atcagctggt ttgtgaacaa cgtggaagta    900

cacacagctc agacacaaac ccatagagag gattacaaca gtactctccg ggtggtcagt    960

gccctcccca tccagcacca ggactggatg agtggcaagg agttcaaatg caaggtcaac   1020

aacaaagacc tcccagcgcc catcgagaga accatctcaa aacccaaagg gtcagtaaga   1080

gcaccacagg tatatgtctt gcctccacca gaagaagaga tgactaagaa acaggtcact   1140

ctgacctgca tggtcacaga cttcatgcct gaagacattt acgtggagtg gaccaacaac   1200

gggaaaacag agctaaacta caagaacact gaaccagtcc tggactctga tggttcttac   1260

ttcatgtaca gcaagctgag agtggaaaag aagaactggg tggaaagaaa tagctactcc   1320

tgttcagtgg tccacgaggg tctgcacaat caccacacga ctaagagctt ctcccggact   1380

ccgggtaaat ga                                                       1392
```

<210> SEQ ID NO 2
<211> LENGTH: 463
<212> TYPE: PRT
<213> ORGANISM: Mus musculus

<400> SEQUENCE: 2

```
Met Glu Trp Ser Trp Val Phe Leu Phe Leu Leu Ser Val Thr Ala Gly
1               5                   10                  15

Val Gln Ser Gln Val Gln Leu Gln Gln Ser Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asp Phe Glu Met His Trp Val Lys Gln Thr Pro Val His Gly Leu
    50                  55                  60
```

```
Glu Trp Ile Gly Asp Ile Asp Pro Gly Thr Gly Asp Thr Ala Tyr Asn
65                  70                  75                  80

Leu Lys Phe Lys Gly Lys Ala Thr Leu Thr Thr Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Leu Gly Ala Phe Val Tyr Trp Gly Gln Gly Thr Leu
        115                 120                 125

Val Thr Val Ser Ala Ala Lys Thr Thr Ala Pro Ser Val Tyr Pro Leu
    130                 135                 140

Ala Pro Val Cys Gly Asp Thr Thr Gly Ser Ser Val Thr Leu Gly Cys
145                 150                 155                 160

Leu Val Lys Gly Tyr Phe Pro Glu Pro Val Thr Leu Thr Trp Asn Ser
                165                 170                 175

Gly Ser Leu Ser Ser Gly Val His Thr Phe Pro Ala Val Leu Gln Ser
            180                 185                 190

Asp Leu Tyr Thr Leu Ser Ser Ser Val Thr Val Thr Ser Ser Thr Trp
        195                 200                 205

Pro Ser Gln Ser Ile Thr Cys Asn Val Ala His Pro Ala Ser Ser Thr
    210                 215                 220

Lys Val Asp Lys Lys Ile Glu Pro Arg Gly Pro Thr Ile Lys Pro Cys
225                 230                 235                 240

Pro Pro Cys Lys Cys Pro Ala Pro Asn Leu Leu Gly Gly Pro Ser Val
                245                 250                 255

Phe Ile Phe Pro Pro Lys Ile Lys Asp Val Leu Met Ile Ser Leu Ser
            260                 265                 270

Pro Ile Val Thr Cys Val Val Val Asp Val Ser Glu Asp Asp Pro Asp
        275                 280                 285

Val Gln Ile Ser Trp Phe Val Asn Asn Val Glu Val His Thr Ala Gln
    290                 295                 300

Thr Gln Thr His Arg Glu Asp Tyr Asn Ser Thr Leu Arg Val Val Ser
305                 310                 315                 320

Ala Leu Pro Ile Gln His Gln Asp Trp Met Ser Gly Lys Glu Phe Lys
                325                 330                 335

Cys Lys Val Asn Asn Lys Asp Leu Pro Ala Pro Ile Glu Arg Thr Ile
            340                 345                 350

Ser Lys Pro Lys Gly Ser Val Arg Ala Pro Gln Val Tyr Val Leu Pro
        355                 360                 365

Pro Pro Glu Glu Glu Met Thr Lys Lys Gln Val Thr Leu Thr Cys Met
    370                 375                 380

Val Thr Asp Phe Met Pro Glu Asp Ile Tyr Val Glu Trp Thr Asn Asn
385                 390                 395                 400

Gly Lys Thr Glu Leu Asn Tyr Lys Asn Thr Glu Pro Val Leu Asp Ser
                405                 410                 415

Asp Gly Ser Tyr Phe Met Tyr Ser Lys Leu Arg Val Glu Lys Lys Asn
            420                 425                 430

Trp Val Glu Arg Asn Ser Tyr Ser Cys Ser Val Val His Glu Gly Leu
        435                 440                 445

His Asn His His Thr Thr Lys Ser Phe Ser Arg Thr Pro Gly Lys
    450                 455                 460
```

<210> SEQ ID NO 3
<211> LENGTH: 720
<212> TYPE: DNA
<213> ORGANISM: Mus musculus -continued

<400> SEQUENCE: 3
atgaatttgc ctgttcatct cttggtgctt ctgttgttct ggattcctgt ttccagaggt 60
gatgttgtgg tgactcaaac tccactctcc ctgcctgtca gctttggaga tcaagtttct 120
atctcttgca ggtctagtca gagtcttgca aacagttatg ggaacaccta tttgtcttgg 180
tacctgcaca agcctggcca gtctccacag ctcctcatct atgggatttc caacagattt 240
tctggggtgc cagacaggtt cagtggcagt ggttcaggga cagatttcac actcaagatc 300
agcacaataa agcctgagga cttgggaatg tattactgtt tacaaggtac acatcagccg 360
tacacgttcg gaggggggac caagctggaa ataaaacggg ccgatgcggc cccaactgta 420
tccatcttcc caccatccag tgagcagtta acatctggag gtgcctcagt cgtgtgcttc 480
ttgaacaact tctaccccaa agacatcaat gtcaagtgga agattgatgg cagtgaacga 540
caaaatggcg tcctgaacag ttggactgat caggacagca aagacagcac ctacagcatg 600
agcagcaccc tcacgttgac caaggacgag tatgaacgac ataacagcta tacctgtgag 660
gccactcaca agacatcaac ttcacccatt gtcaagagct tcaacaggaa tgagtgttga 720

<210> SEQ ID NO 4
<211> LENGTH: 239
<212> TYPE: PRT
<213> ORGANISM: Mus musculus

<400> SEQUENCE: 4

Met Asn Leu Pro Val His Leu Leu Val Leu Leu Leu Phe Trp Ile Pro
1 5 10 15

Val Ser Arg Gly Asp Val Val Val Thr Gln Thr Pro Leu Ser Leu Pro
20 25 30

Val Ser Phe Gly Asp Gln Val Ser Ile Ser Cys Arg Ser Ser Gln Ser
35 40 45

Leu Ala Asn Ser Tyr Gly Asn Thr Tyr Leu Ser Trp Tyr Leu His Lys
50 55 60

Pro Gly Gln Ser Pro Gln Leu Leu Ile Tyr Gly Ile Ser Asn Arg Phe
65 70 75 80

Ser Gly Val Pro Asp Arg Phe Ser Gly Ser Gly Ser Gly Thr Asp Phe
85 90 95

Thr Leu Lys Ile Ser Thr Ile Lys Pro Glu Asp Leu Gly Met Tyr Tyr
100 105 110

Cys Leu Gln Gly Thr His Gln Pro Tyr Thr Phe Gly Gly Gly Thr Lys
115 120 125

Leu Glu Ile Lys Arg Ala Asp Ala Ala Pro Thr Val Ser Ile Phe Pro
130 135 140

Pro Ser Ser Glu Gln Leu Thr Ser Gly Gly Ala Ser Val Val Cys Phe
145 150 155 160

Leu Asn Asn Phe Tyr Pro Lys Asp Ile Asn Val Lys Trp Lys Ile Asp
165 170 175

Gly Ser Glu Arg Gln Asn Gly Val Leu Asn Ser Trp Thr Asp Gln Asp
180 185 190

Ser Lys Asp Ser Thr Tyr Ser Met Ser Ser Thr Leu Thr Leu Thr Lys
195 200 205

Asp Glu Tyr Glu Arg His Asn Ser Tyr Thr Cys Glu Ala Thr His Lys
210 215 220

Thr Ser Thr Ser Pro Ile Val Lys Ser Phe Asn Arg Asn Glu Cys
225 230 235

<210> SEQ ID NO 5
<211> LENGTH: 1392
<212> TYPE: DNA
<213> ORGANISM: Artificial
<220> FEATURE:
<223> OTHER INFORMATION: An artificially synthesized nucleotide sequence

<400> SEQUENCE: 5
atggaatgga gctgggtctt tctcttcctc ctgtcagtaa ctgcaggtgt ccaatcccag 60
gttcaactgc agcagtctgg ggctgagctg gtgaggcctg gggcttcagt gaagctgtcc 120
tgcaaggctt cgggctacac attttctgac tttgaaatgc actgggtgaa gcagacacct 180
gtgcatggcc tggaatggat tggagatatt gatcctggaa ctggtgatac tgcctacaat 240
ctgaagttca agggcaaggc cacactgact acagacaaat cttccagcac agcctacatg 300
gagctccgca gcctgacatc tgaggactct gccgtctatt actgtaccct cggggccttt 360
gtttactggg gccaagggac tctggtcact gtctctgcag ctagcaccaa gggcccatcg 420
gtcttccccc tggcaccctc ctccaagagc acctctgggg gcacagcggc cctgggctgc 480
ctggtcaagg actacttccc cgaaccggtg acggtgtcgt ggaactcagg cgccctgacc 540
agcggcgtgc acaccttccc ggctgtccta cagtcctcag gactctactc cctcagcagc 600
gtggtgaccg tgccctccag cagcttgggc acccagacct acatctgcaa cgtgaatcac 660
aagcccagca acaccaaggt ggacaagaaa gttgagccca aatcttgtga caaaactcac 720
acatgcccac cgtgcccagc acctgaactc ctggggggac cgtcagtctt cctcttcccc 780
ccaaaaccca aggacaccct catgatctcc cggacccctg aggtcacatg cgtggtggtg 840
gacgtgagcc acgaagaccc tgaggtcaag ttcaactggt acgtggacgg cgtggaggtg 900
cataatgcca agacaaagcc gcgggaggag cagtacaaca gcacgtaccg tgtggtcagc 960
gtcctcaccg tcctgcacca ggactggctg aatggcaagg agtacaagtg caaggtctcc 1020
aacaaagccc tcccagcccc catcgagaaa accatctcca aagccaaagg gcagccccga 1080
gaaccacagg tgtacaccct gcccccatcc cgggatgagc tgaccaagaa ccaggtcagc 1140
ctgacctgcc tggtcaaagg cttctatccc agcgacatcg ccgtggagtg ggagagcaat 1200
gggcagccgg agaacaacta caagaccacg cctcccgtgc tggactccga cggctccttc 1260
ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaat ga 1392

<210> SEQ ID NO 6
<211> LENGTH: 463
<212> TYPE: PRT
<213> ORGANISM: artificial
<220> FEATURE:
<223> OTHER INFORMATION: An artificially synthesized polypeptide
sequence

<400> SEQUENCE: 6

Met Glu Trp Ser Trp Val Phe Leu Phe Leu Leu Ser Val Thr Ala Gly
1 5 10 15

Val Gln Ser Gln Val Gln Leu Gln Gln Ser Gly Ala Glu Leu Val Arg
20 25 30

Pro Gly Ala Ser Val Lys Leu Ser Cys Lys Ala Ser Gly Tyr Thr Phe
35 40 45

Ser Asp Phe Glu Met His Trp Val Lys Gln Thr Pro Val His Gly Leu
50 55 60

```
Glu Trp Ile Gly Asp Ile Asp Pro Gly Thr Gly Asp Thr Ala Tyr Asn
65                  70                  75                  80

Leu Lys Phe Lys Gly Lys Ala Thr Leu Thr Thr Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Thr Leu Gly Ala Phe Val Tyr Trp Gly Gln Gly Thr Leu
        115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Asp Glu Leu Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 7
<211> LENGTH: 720
<212> TYPE: DNA

```
<213> ORGANISM: artificial
<220> FEATURE:
<223> OTHER INFORMATION: An artificially synthesized nucleotide sequence

<400> SEQUENCE: 7

atgaatttgc ctgttcatct cttggtgctt ctgttgttct ggattcctgt ttccagaggt     60

gatgttgtgg tgactcaaac tccactctcc ctgcctgtca gctttggaga tcaagtttct    120

atctcttgca ggtctagtca gagtcttgca aacagttatg ggaacaccta tttgtcttgg    180

tacctgcaca agcctggcca gtctccacag ctcctcatct atgggatttc caacagattt    240

tctggggtgc cagacaggtt cagtggcagt ggttcaggga cagatttcac actcaagatc    300

agcacaataa agcctgagga cttgggaatg tattactgtt tacaaggtac acatcagccg    360

tacacgttcg gaggggggac caagctggaa ataaaacgta cggtggctgc accatctgtc    420

ttcatcttcc cgccatctga tgagcagttg aaatctggaa ctgcctctgt tgtgtgcctg    480

ctgaataact tctatcccag agaggccaaa gtacagtgga aggtggataa cgccctccaa    540

tcgggtaact cccaggagag tgtcacagag caggacagca aggacagcac ctacagcctc    600

agcagcaccc tgacgctgag caaagcagac tacgagaaac acaaagtcta cgcctgcgaa    660

gtcacccatc agggcctgag ctcgcccgtc acaaagagct tcaacagggg agagtgttga    720


<210> SEQ ID NO 8
<211> LENGTH: 239
<212> TYPE: PRT
<213> ORGANISM: artificial
<220> FEATURE:
<223> OTHER INFORMATION: An artificially synthesized polypeptide
      sequence

<400> SEQUENCE: 8

Met Asn Leu Pro Val His Leu Leu Val Leu Leu Leu Phe Trp Ile Pro
1               5                   10                  15

Val Ser Arg Gly Asp Val Val Val Thr Gln Thr Pro Leu Ser Leu Pro
            20                  25                  30

Val Ser Phe Gly Asp Gln Val Ser Ile Ser Cys Arg Ser Ser Gln Ser
        35                  40                  45

Leu Ala Asn Ser Tyr Gly Asn Thr Tyr Leu Ser Trp Tyr Leu His Lys
    50                  55                  60

Pro Gly Gln Ser Pro Gln Leu Leu Ile Tyr Gly Ile Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Thr Ile Lys Pro Glu Asp Leu Gly Met Tyr Tyr
            100                 105                 110

Cys Leu Gln Gly Thr His Gln Pro Tyr Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205
```

-continued

```
Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 9
<211> LENGTH: 342
<212> TYPE: DNA
<213> ORGANISM: Mus musculus

<400> SEQUENCE: 9

caggttcaac tgcagcagtc tggggctgag ctggtgaggc ctggggcttc agtgaagctg      60

tcctgcaagg cttcgggcta cacattttct gactttgaaa tgcactgggt gaagcagaca     120

cctgtgcatg gcctggaatg gattggagat attgatcctg gaactggtga tactgcctac     180

aatctgaagt tcaagggcaa ggccacactg actacagaca aatcttccag cacagcctac     240

atggagctcc gcagcctgac atctgaggac tctgccgtct attactgtac cctcggggcc     300

tttgtttact ggggccaagg gactctggtc actgtctctg ca                        342


<210> SEQ ID NO 10
<211> LENGTH: 114
<212> TYPE: PRT
<213> ORGANISM: Mus musculus

<400> SEQUENCE: 10

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Ser Asp Phe
            20                  25                  30

Glu Met His Trp Val Lys Gln Thr Pro Val His Gly Leu Glu Trp Ile
        35                  40                  45

Gly Asp Ile Asp Pro Gly Thr Gly Asp Thr Ala Tyr Asn Leu Lys Phe
    50                  55                  60

Lys Gly Lys Ala Thr Leu Thr Thr Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Leu Gly Ala Phe Val Tyr Trp Gly Gln Gly Thr Leu Val Thr Val
            100                 105                 110

Ser Ala


<210> SEQ ID NO 11
<211> LENGTH: 15
<212> TYPE: DNA
<213> ORGANISM: Mus musculus

<400> SEQUENCE: 11

gactttgaaa tgcac                                                       15


<210> SEQ ID NO 12
<211> LENGTH: 5
<212> TYPE: PRT
<213> ORGANISM: Mus musculus

<400> SEQUENCE: 12

Asp Phe Glu Met His
1               5


<210> SEQ ID NO 13
```

<211> LENGTH: 51
<212> TYPE: DNA
<213> ORGANISM: Mus musculus

<400> SEQUENCE: 13
gatattgatc ctggaactgg tgatactgcc tacaatctga agttcaaggg c 51

<210> SEQ ID NO 14
<211> LENGTH: 17
<212> TYPE: PRT
<213> ORGANISM: Mus musculus

<400> SEQUENCE: 14

Asp Ile Asp Pro Gly Thr Gly Asp Thr Ala Tyr Asn Leu Lys Phe Lys
1 5 10 15

Gly

<210> SEQ ID NO 15
<211> LENGTH: 15
<212> TYPE: DNA
<213> ORGANISM: Mus musculus

<400> SEQUENCE: 15
ggggcctttg tttac 15

<210> SEQ ID NO 16
<211> LENGTH: 5
<212> TYPE: PRT
<213> ORGANISM: Mus musculus

<400> SEQUENCE: 16

Gly Ala Phe Val Tyr
1 5

<210> SEQ ID NO 17
<211> LENGTH: 339
<212> TYPE: DNA
<213> ORGANISM: Mus musculus

<400> SEQUENCE: 17
gatgttgtgg tgactcaaac tccactctcc ctgcctgtca gctttggaga tcaagtttct 60
atctcttgca ggtctagtca gagtcttgca aacagttatg ggaacaccta tttgtcttgg 120
tacctgcaca agcctggcca gtctccacag ctcctcatct atgggatttc caacagattt 180
tctggggtgc cagacaggtt cagtggcagt ggttcaggga cagatttcac actcaagatc 240
agcacaataa agcctgagga cttgggaatg tattactgtt tacaaggtac acatcagccg 300
tacacgttcg gaggggggac caagctggaa ataaaacgg 339

<210> SEQ ID NO 18
<211> LENGTH: 113
<212> TYPE: PRT
<213> ORGANISM: Mus musculus

<400> SEQUENCE: 18

Asp Val Val Val Thr Gln Thr Pro Leu Ser Leu Pro Val Ser Phe Gly
1 5 10 15

Asp Gln Val Ser Ile Ser Cys Arg Ser Ser Gln Ser Leu Ala Asn Ser
20 25 30

Tyr Gly Asn Thr Tyr Leu Ser Trp Tyr Leu His Lys Pro Gly Gln Ser
35 40 45

Pro Gln Leu Leu Ile Tyr Gly Ile Ser Asn Arg Phe Ser Gly Val Pro

```
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Leu Gln Gly
                85                  90                  95

Thr His Gln Pro Tyr Thr Phe Gly Gly Gly Thr Lys Leu Glu Ile Lys
            100                 105                 110

Arg


<210> SEQ ID NO 19
<211> LENGTH: 48
<212> TYPE: DNA
<213> ORGANISM: Mus musculus

<400> SEQUENCE: 19

aggtctagtc agagtcttgc aaacagttat gggaacacct atttgtct                  48


<210> SEQ ID NO 20
<211> LENGTH: 16
<212> TYPE: PRT
<213> ORGANISM: Mus musculus

<400> SEQUENCE: 20

Arg Ser Ser Gln Ser Leu Ala Asn Ser Tyr Gly Asn Thr Tyr Leu Ser
1               5                   10                  15


<210> SEQ ID NO 21
<211> LENGTH: 21
<212> TYPE: DNA
<213> ORGANISM: Mus musculus

<400> SEQUENCE: 21

gggatttcca acagattttc t                                               21


<210> SEQ ID NO 22
<211> LENGTH: 7
<212> TYPE: PRT
<213> ORGANISM: Mus musculus

<400> SEQUENCE: 22

Gly Ile Ser Asn Arg Phe Ser
1               5


<210> SEQ ID NO 23
<211> LENGTH: 27
<212> TYPE: DNA
<213> ORGANISM: Mus musculus

<400> SEQUENCE: 23

ttacaaggta cacatcagcc gtacacg                                         27


<210> SEQ ID NO 24
<211> LENGTH: 9
<212> TYPE: PRT
<213> ORGANISM: Mus musculus

<400> SEQUENCE: 24

Leu Gln Gly Thr His Gln Pro Tyr Thr
1               5


<210> SEQ ID NO 25
<211> LENGTH: 28
<212> TYPE: DNA
```

<213> ORGANISM: artificial
<220> FEATURE:
<223> OTHER INFORMATION: An artificailly synthesized primer sequence

<400> SEQUENCE: 25
ccatggagtt agtttgggca gcagatcc 28

<210> SEQ ID NO 26
<211> LENGTH: 27
<212> TYPE: DNA
<213> ORGANISM: artificial
<220> FEATURE:
<223> OTHER INFORMATION: An artificially synthesized primer sequence

<400> SEQUENCE: 26
ggcacctcca gatgttaact gctcact 27

<210> SEQ ID NO 27
<211> LENGTH: 35
<212> TYPE: DNA
<213> ORGANISM: artificial
<220> FEATURE:
<223> OTHER INFORMATION: An artificially synthesized primer sequence

<400> SEQUENCE: 27
cttgaattcc accatggaat ggagctgggt ctttc 35

<210> SEQ ID NO 28
<211> LENGTH: 32
<212> TYPE: DNA
<213> ORGANISM: artificial
<220> FEATURE:
<223> OTHER INFORMATION: An artificially synthesized primer sequence

<400> SEQUENCE: 28
cgcgctagct gcagagacag tgaccagagt cc 32

<210> SEQ ID NO 29
<211> LENGTH: 35
<212> TYPE: DNA
<213> ORGANISM: artificial
<220> FEATURE:
<223> OTHER INFORMATION: An artificially synthesized primer sequence

<400> SEQUENCE: 29
cagggatcca ccatgaattt gcctgttcat ctctt 35

<210> SEQ ID NO 30
<211> LENGTH: 30
<212> TYPE: DNA
<213> ORGANISM: artificial
<220> FEATURE:
<223> OTHER INFORMATION: An artificially synthesized primer sequence

<400> SEQUENCE: 30
cggcgtacgt tttatttcca gcttggtccc 30

<210> SEQ ID NO 31
<211> LENGTH: 1392
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(1389)
<220> FEATURE:
<221> NAME/KEY: sig_peptide

```
<222> LOCATION: (1)..(57)
<220> FEATURE:
<221> NAME/KEY: mat_peptide
<222> LOCATION: (58)..(1389)

<400> SEQUENCE: 31

atg gac tgg acc tgg agc atc ctt ttc ttg gtg gca gca gca aca ggt       48
Met Asp Trp Thr Trp Ser Ile Leu Phe Leu Val Ala Ala Ala Thr Gly
                -15                 -10                 -5

gcc cac tcc cag gtt cag ctg gtg cag tct gga gct gag gtg aag aag       96
Ala His Ser Gln Val Gln Leu Val Gln Ser Gly Ala Glu Val Lys Lys
        -1  1               5                   10

cct ggg gcc tca gtg aag gtc tcc tgc aag gct tct ggt tac acc ttt      144
Pro Gly Ala Ser Val Lys Val Ser Cys Lys Ala Ser Gly Tyr Thr Phe
    15                  20                  25

acc gac ttt gaa atg cac tgg gtg cga cag gcc cct gga caa ggg ctt      192
Thr Asp Phe Glu Met His Trp Val Arg Gln Ala Pro Gly Gln Gly Leu
30                  35                  40                  45

gag tgg atg gga gat att gat cct gga act ggt gat act gcc tac aat      240
Glu Trp Met Gly Asp Ile Asp Pro Gly Thr Gly Asp Thr Ala Tyr Asn
                50                  55                  60

ctg aag ttc aag ggc aga gtc acc atg acc aca gac aca tcc acg agc      288
Leu Lys Phe Lys Gly Arg Val Thr Met Thr Thr Asp Thr Ser Thr Ser
            65                  70                  75

aca gcc tac atg gag ctg agg agc ctg aga tct gac gac acg gcc gtg      336
Thr Ala Tyr Met Glu Leu Arg Ser Leu Arg Ser Asp Asp Thr Ala Val
        80                  85                  90

tat tac tgt gcg ttg ggg gcc ttt gtt tac tgg ggc cag gga acc ctg      384
Tyr Tyr Cys Ala Leu Gly Ala Phe Val Tyr Trp Gly Gln Gly Thr Leu
    95                  100                 105

gtc acc gtc tcc tca gct agc acc aag ggc cca tcg gtc ttc ccc ctg      432
Val Thr Val Ser Ser Ala Ser Thr Lys Gly Pro Ser Val Phe Pro Leu
110                 115                 120                 125

gca ccc tcc tcc aag agc acc tct ggg ggc aca gcg gcc ctg ggc tgc      480
Ala Pro Ser Ser Lys Ser Thr Ser Gly Gly Thr Ala Ala Leu Gly Cys
                130                 135                 140

ctg gtc aag gac tac ttc ccc gaa ccg gtg acg gtg tcg tgg aac tca      528
Leu Val Lys Asp Tyr Phe Pro Glu Pro Val Thr Val Ser Trp Asn Ser
            145                 150                 155

ggc gcc ctg acc agc ggc gtg cac acc ttc ccg gct gtc cta cag tcc      576
Gly Ala Leu Thr Ser Gly Val His Thr Phe Pro Ala Val Leu Gln Ser
        160                 165                 170

tca gga ctc tac tcc ctc agc agc gtg gtg acc gtg ccc tcc agc agc      624
Ser Gly Leu Tyr Ser Leu Ser Ser Val Val Thr Val Pro Ser Ser Ser
    175                 180                 185

ttg ggc acc cag acc tac atc tgc aac gtg aat cac aag ccc agc aac      672
Leu Gly Thr Gln Thr Tyr Ile Cys Asn Val Asn His Lys Pro Ser Asn
190                 195                 200                 205

acc aag gtg gac aag aaa gtt gag ccc aaa tct tgt gac aaa act cac      720
Thr Lys Val Asp Lys Lys Val Glu Pro Lys Ser Cys Asp Lys Thr His
                210                 215                 220

aca tgc cca ccg tgc cca gca cct gaa ctc ctg ggg gga ccg tca gtc      768
Thr Cys Pro Pro Cys Pro Ala Pro Glu Leu Leu Gly Gly Pro Ser Val
            225                 230                 235

ttc ctc ttc ccc cca aaa ccc aag gac acc ctc atg atc tcc cgg acc      816
Phe Leu Phe Pro Pro Lys Pro Lys Asp Thr Leu Met Ile Ser Arg Thr
        240                 245                 250

cct gag gtc aca tgc gtg gtg gtg gac gtg agc cac gaa gac cct gag      864
Pro Glu Val Thr Cys Val Val Val Asp Val Ser His Glu Asp Pro Glu
    255                 260                 265

gtc aag ttc aac tgg tac gtg gac ggc gtg gag gtg cat aat gcc aag      912
```

```
Val Lys Phe Asn Trp Tyr Val Asp Gly Val Glu Val His Asn Ala Lys
270                 275                 280                 285

aca aag ccg cgg gag gag cag tac aac agc acg tac cgt gtg gtc agc      960
Thr Lys Pro Arg Glu Glu Gln Tyr Asn Ser Thr Tyr Arg Val Val Ser
                290                 295                 300

gtc ctc acc gtc ctg cac cag gac tgg ctg aat ggc aag gag tac aag     1008
Val Leu Thr Val Leu His Gln Asp Trp Leu Asn Gly Lys Glu Tyr Lys
            305                 310                 315

tgc aag gtc tcc aac aaa gcc ctc cca gcc ccc atc gag aaa acc atc     1056
Cys Lys Val Ser Asn Lys Ala Leu Pro Ala Pro Ile Glu Lys Thr Ile
        320                 325                 330

tcc aaa gcc aaa ggg cag ccc cga gaa cca cag gtg tac acc ctg ccc     1104
Ser Lys Ala Lys Gly Gln Pro Arg Glu Pro Gln Val Tyr Thr Leu Pro
    335                 340                 345

cca tcc cgg gat gag ctg acc aag aac cag gtc agc ctg acc tgc ctg     1152
Pro Ser Arg Asp Glu Leu Thr Lys Asn Gln Val Ser Leu Thr Cys Leu
350                 355                 360                 365

gtc aaa ggc ttc tat ccc agc gac atc gcc gtg gag tgg gag agc aat     1200
Val Lys Gly Phe Tyr Pro Ser Asp Ile Ala Val Glu Trp Glu Ser Asn
                370                 375                 380

ggg cag ccg gag aac aac tac aag acc acg cct ccc gtg ctg gac tcc     1248
Gly Gln Pro Glu Asn Asn Tyr Lys Thr Thr Pro Pro Val Leu Asp Ser
            385                 390                 395

gac ggc tcc ttc ttc ctc tac agc aag ctc acc gtg gac aag agc agg     1296
Asp Gly Ser Phe Phe Leu Tyr Ser Lys Leu Thr Val Asp Lys Ser Arg
        400                 405                 410

tgg cag cag ggg aac gtc ttc tca tgc tcc gtg atg cat gag gct ctg     1344
Trp Gln Gln Gly Asn Val Phe Ser Cys Ser Val Met His Glu Ala Leu
    415                 420                 425

cac aac cac tac acg cag aag agc ctc tcc ctg tct ccg ggt aaa tga     1392
His Asn His Tyr Thr Gln Lys Ser Leu Ser Leu Ser Pro Gly Lys
430                 435                 440


<210> SEQ ID NO 32
<211> LENGTH: 463
<212> TYPE: PRT
<213> ORGANISM: Artificial
<220> FEATURE:
<223> OTHER INFORMATION: Synthetic Construct

<400> SEQUENCE: 32

Met Asp Trp Thr Trp Ser Ile Leu Phe Leu Val Ala Ala Ala Thr Gly
                -15                 -10                 -5

Ala His Ser Gln Val Gln Leu Val Gln Ser Gly Ala Glu Val Lys Lys
        -1  1               5                   10

Pro Gly Ala Ser Val Lys Val Ser Cys Lys Ala Ser Gly Tyr Thr Phe
    15                  20                  25

Thr Asp Phe Glu Met His Trp Val Arg Gln Ala Pro Gly Gln Gly Leu
30                  35                  40                  45

Glu Trp Met Gly Asp Ile Asp Pro Gly Thr Gly Asp Thr Ala Tyr Asn
                50                  55                  60

Leu Lys Phe Lys Gly Arg Val Thr Met Thr Thr Asp Thr Ser Thr Ser
            65                  70                  75

Thr Ala Tyr Met Glu Leu Arg Ser Leu Arg Ser Asp Asp Thr Ala Val
        80                  85                  90

Tyr Tyr Cys Ala Leu Gly Ala Phe Val Tyr Trp Gly Gln Gly Thr Leu
    95                  100                 105

Val Thr Val Ser Ser Ala Ser Thr Lys Gly Pro Ser Val Phe Pro Leu
110                 115                 120                 125
```

-continued

```
Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
            145                 150                 155

Gly Ala Leu Thr Ser Gly Val His Thr Phe Pro Ala Val Leu Gln Ser
        160                 165                 170

Ser Gly Leu Tyr Ser Leu Ser Ser Val Val Thr Val Pro Ser Ser Ser
    175                 180                 185

Leu Gly Thr Gln Thr Tyr Ile Cys Asn Val Asn His Lys Pro Ser Asn
190                 195                 200                 205

Thr Lys Val Asp Lys Lys Val Glu Pro Lys Ser Cys Asp Lys Thr His
                210                 215                 220

Thr Cys Pro Pro Cys Pro Ala Pro Glu Leu Leu Gly Gly Pro Ser Val
            225                 230                 235

Phe Leu Phe Pro Pro Lys Pro Lys Asp Thr Leu Met Ile Ser Arg Thr
        240                 245                 250

Pro Glu Val Thr Cys Val Val Val Asp Val Ser His Glu Asp Pro Glu
    255                 260                 265

Val Lys Phe Asn Trp Tyr Val Asp Gly Val Glu Val His Asn Ala Lys
270                 275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
            305                 310                 315

Cys Lys Val Ser Asn Lys Ala Leu Pro Ala Pro Ile Glu Lys Thr Ile
        320                 325                 330

Ser Lys Ala Lys Gly Gln Pro Arg Glu Pro Gln Val Tyr Thr Leu Pro
    335                 340                 345

Pro Ser Arg Asp Glu Leu Thr Lys Asn Gln Val Ser Leu Thr Cys Leu
350                 355                 360                 365

Val Lys Gly Phe Tyr Pro Ser Asp Ile Ala Val Glu Trp Glu Ser Asn
                370                 375                 380

Gly Gln Pro Glu Asn Asn Tyr Lys Thr Thr Pro Pro Val Leu Asp Ser
            385                 390                 395

Asp Gly Ser Phe Phe Leu Tyr Ser Lys Leu Thr Val Asp Lys Ser Arg
        400                 405                 410

Trp Gln Gln Gly Asn Val Phe Ser Cys Ser Val Met His Glu Ala Leu
    415                 420                 425

His Asn His Tyr Thr Gln Lys Ser Leu Ser Leu Ser Pro Gly Lys
430                 435                 440


<210> SEQ ID NO 33
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 33

atg aaa tac cta ttg cct acg gca gcc gct gga ttg tta tta ctc gcg       48
```

```
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5                  -1  1               5                   10

ctg ccc gtc acc cct gga gag ccg gcc tcc atc tcc tgc agg tct agt      144
Leu Pro Val Thr Pro Gly Glu Pro Ala Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 34
<211> LENGTH: 241
<212> TYPE: PRT
<213> ORGANISM: Artificial
<220> FEATURE:
<223> OTHER INFORMATION: Synthetic Construct

<400> SEQUENCE: 34

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5                  -1  1               5                   10

Leu Pro Val Thr Pro Gly Glu Pro Ala Ser Ile Ser Cys Arg Ser Ser
                15                  20                  25
```

```
Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 35
<211> LENGTH: 720
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(717)
<220> FEATURE:
<221> NAME/KEY: sig_peptide
<222> LOCATION: (1)..(60)
<220> FEATURE:
<221> NAME/KEY: mat_peptide
<222> LOCATION: (61)..(717)

<400> SEQUENCE: 35

atg aat ttg cct gtt cat ctc ttg gtg ctt ctg ttg ttc tgg att cct       48
Met Asn Leu Pro Val His Leu Leu Val Leu Leu Leu Phe Trp Ile Pro
-20                 -15                 -10                 -5

gtt tcc aga ggt gat gtt gtg gtg act caa act cca ctc tcc ctg cct       96
Val Ser Arg Gly Asp Val Val Val Thr Gln Thr Pro Leu Ser Leu Pro
            -1  1               5                   10

gtc agc ttt gga gat caa gtt tct atc tct tgc agg tct agt cag agt      144
Val Ser Phe Gly Asp Gln Val Ser Ile Ser Cys Arg Ser Ser Gln Ser
        15                  20                  25

ctt gca aac agt tat ggg aac acc tat ttg tct tgg tac ctg cag aag      192
Leu Ala Asn Ser Tyr Gly Asn Thr Tyr Leu Ser Trp Tyr Leu Gln Lys
    30                  35                  40

cca ggg cag tct cca cag ctc ctg atc tat ggg att tcc aac aga ttt      240
Pro Gly Gln Ser Pro Gln Leu Leu Ile Tyr Gly Ile Ser Asn Arg Phe
45                  50                  55                  60

tct ggg gtc cct gac agg ttc agt ggc agt gga tca ggc aca gat ttt      288
Ser Gly Val Pro Asp Arg Phe Ser Gly Ser Gly Ser Gly Thr Asp Phe
```

-continued

```
                65                  70                  75

aca ctg aaa atc agc aga gtg gag gct gag gat gtt ggg gtt tat tac      336
Thr Leu Lys Ile Ser Arg Val Glu Ala Glu Asp Val Gly Val Tyr Tyr
            80                  85                  90

tgc tta caa ggt aca cat cag ccg tac acg ttt ggc cag ggg acc aag      384
Cys Leu Gln Gly Thr His Gln Pro Tyr Thr Phe Gly Gln Gly Thr Lys
        95                  100                 105

ctg gag atc aaa cgt acg gtg gct gca cca tct gtc ttc atc ttc ccg      432
Leu Glu Ile Lys Arg Thr Val Ala Ala Pro Ser Val Phe Ile Phe Pro
    110                 115                 120

cca tct gat gag cag ttg aaa tct gga act gcc tct gtt gtg tgc ctg      480
Pro Ser Asp Glu Gln Leu Lys Ser Gly Thr Ala Ser Val Val Cys Leu
125                 130                 135                 140

ctg aat aac ttc tat ccc aga gag gcc aaa gta cag tgg aag gtg gat      528
Leu Asn Asn Phe Tyr Pro Arg Glu Ala Lys Val Gln Trp Lys Val Asp
                145                 150                 155

aac gcc ctc caa tcg ggt aac tcc cag gag agt gtc aca gag cag gac      576
Asn Ala Leu Gln Ser Gly Asn Ser Gln Glu Ser Val Thr Glu Gln Asp
            160                 165                 170

agc aag gac agc acc tac agc ctc agc agc acc ctg acg ctg agc aaa      624
Ser Lys Asp Ser Thr Tyr Ser Leu Ser Ser Thr Leu Thr Leu Ser Lys
        175                 180                 185

gca gac tac gag aaa cac aaa gtc tac gcc tgc gaa gtc acc cat cag      672
Ala Asp Tyr Glu Lys His Lys Val Tyr Ala Cys Glu Val Thr His Gln
    190                 195                 200

ggc ctg agc tcg ccc gtc aca aag agc ttc aac agg gga gag tgt tga      720
Gly Leu Ser Ser Pro Val Thr Lys Ser Phe Asn Arg Gly Glu Cys
205                 210                 215


<210> SEQ ID NO 36
<211> LENGTH: 239
<212> TYPE: PRT
<213> ORGANISM: Artificial
<220> FEATURE:
<223> OTHER INFORMATION: Synthetic Construct

<400> SEQUENCE: 36

Met Asn Leu Pro Val His Leu Leu Val Leu Leu Leu Phe Trp Ile Pro
-20                 -15                 -10                 -5

Val Ser Arg Gly Asp Val Val Val Thr Gln Thr Pro Leu Ser Leu Pro
            -1  1               5                   10

Val Ser Phe Gly Asp Gln Val Ser Ile Ser Cys Arg Ser Ser Gln Ser
        15                  20                  25

Leu Ala Asn Ser Tyr Gly Asn Thr Tyr Leu Ser Trp Tyr Leu Gln Lys
    30                  35                  40

Pro Gly Gln Ser Pro Gln Leu Leu Ile Tyr Gly Ile Ser Asn Arg Phe
45                  50                  55                  60

Ser Gly Val Pro Asp Arg Phe Ser Gly Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Leu Gln Gly Thr His Gln Pro Tyr Thr Phe Gly Gln Gly Thr Lys
        95                  100                 105

Leu Glu Ile Lys Arg Thr Val Ala Ala Pro Ser Val Phe Ile Phe Pro
    110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155
```

```
Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
    190                 195                 200

Gly Leu Ser Ser Pro Val Thr Lys Ser Phe Asn Arg Gly Glu Cys
205                 210                 215


<210> SEQ ID NO 37
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 37

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc cct gga gag ccg gcc tcc atc tcc tgc agg tct agt      144
Leu Pro Val Thr Pro Gly Glu Pro Ala Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cac aag cct ggc cag tct cca cag ctc ctc atc tat ggg att tcc aac      240
His Lys Pro Gly Gln Ser Pro Gln Leu Leu Ile Tyr Gly Ile Ser Asn
        45                  50                  55

aga ttt tct ggg gtg cca gac agg ttc agt ggc agt ggt tca ggg aca      288
Arg Phe Ser Gly Val Pro Asp Arg Phe Ser Gly Ser Gly Ser Gly Thr
    60                  65                  70

gat ttc aca ctc aag atc agc aca ata aag cct gag gac ttg gga atg      336
Asp Phe Thr Leu Lys Ile Ser Thr Ile Lys Pro Glu Asp Leu Gly Met
75                  80                  85                  90

tat tac tgt tta caa ggt aca cat cag ccg tac acg ttc gga ggg ggg      384
Tyr Tyr Cys Leu Gln Gly Thr His Gln Pro Tyr Thr Phe Gly Gly Gly
                95                  100                 105

acc aag ctg gaa ata aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170
```

```
cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 38
<211> LENGTH: 241
<212> TYPE: PRT
<213> ORGANISM: Artificial
<220> FEATURE:
<223> OTHER INFORMATION: Synthetic Construct

<400> SEQUENCE: 38

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Pro Gly Glu Pro Ala Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

His Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Thr Ile Lys Pro Glu Asp Leu Gly Met
75                  80                  85                  90

Tyr Tyr Cys Leu Gln Gly Thr His Gln Pro Tyr Thr Phe Gly Gly Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 39
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
```

```
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 39

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg gtg act cag tct cca ctc tcc       96
Ala Gln Pro Ala Met Ala Asp Val Val Val Thr Gln Ser Pro Leu Ser
    -5              -1  1               5                   10

ctg ccc gtc acc cct gga gag ccg gcc tcc atc tcc tgc agg tct agt      144
Leu Pro Val Thr Pro Gly Glu Pro Ala Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 40
<211> LENGTH: 241
<212> TYPE: PRT
<213> ORGANISM: Artificial
<220> FEATURE:
```

```
<223> OTHER INFORMATION: Synthetic Construct

<400> SEQUENCE: 40

Met Lys Tyr Leu Leu Pro Thr Ala Ala Ala Gly Leu Leu Leu Leu Ala
        -20                 -15                 -10

Ala Gln Pro Ala Met Ala Asp Val Val Val Thr Gln Ser Pro Leu Ser
    -5              -1  1               5                   10

Leu Pro Val Thr Pro Gly Glu Pro Ala Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 41
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 41

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc ttt gga gag ccg gcc tcc atc tcc tgc agg tct agt      144
Leu Pro Val Thr Phe Gly Glu Pro Ala Ser Ile Ser Cys Arg Ser Ser
```

-continued 15                  20                  25 cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40 cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55 aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70 gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90 tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105 acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120 ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135 tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150 gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170 cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185 agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200 cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215 tgt tga                                                              726
Cys

<210> SEQ ID NO 42
<211> LENGTH: 241
<212> TYPE: PRT
<213> ORGANISM: Artificial
<220> FEATURE:
<223> OTHER INFORMATION: Synthetic Construct

<400> SEQUENCE: 42

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Phe Gly Glu Pro Ala Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

```
Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 43
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 43

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5                  -1  1               5                   10

ctg ccc gtc acc cct gga gag caa gcc tcc atc tcc tgc agg tct agt      144
Leu Pro Val Thr Pro Gly Glu Gln Ala Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105
```

```
acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 44
<211> LENGTH: 241
<212> TYPE: PRT
<213> ORGANISM: Artificial
<220> FEATURE:
<223> OTHER INFORMATION: Synthetic Construct

<400> SEQUENCE: 44

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Pro Gly Glu Gln Ala Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185
```

```
Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 45
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 45

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc ttt gga gag caa gcc tcc atc tcc tgc agg tct agt      144
Leu Pro Val Thr Phe Gly Glu Gln Ala Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185
```

-continued

```
agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 46
<211> LENGTH: 241
<212> TYPE: PRT
<213> ORGANISM: Artificial
<220> FEATURE:
<223> OTHER INFORMATION: Synthetic Construct

<400> SEQUENCE: 46

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Phe Gly Glu Gln Ala Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 47
<211> LENGTH: 726
<212> TYPE: DNA
<213> ORGANISM: Artificial
 <220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
```

```
<222> LOCATION: (1)..(66)
<220> FEATURE:
<221> NAME/KEY: mat_peptide
<222> LOCATION: (67)..(723)

<400> SEQUENCE: 47

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc cct gga gag ccg gtc tcc atc tcc tgc agg tct agt      144
Leu Pro Val Thr Pro Gly Glu Pro Val Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 48
<211> LENGTH: 241
<212> TYPE: PRT
<213> ORGANISM: Artificial
<220> FEATURE:
<223> OTHER INFORMATION: Synthetic Construct

<400> SEQUENCE: 48
```

-continued

```
Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Pro Gly Glu Pro Val Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 49
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 49

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc ttt gga gag ccg gtc tcc atc tcc tgc agg tct agt      144
Leu Pro Val Thr Phe Gly Glu Pro Val Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
```

```
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120

ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 50
<211> LENGTH: 241
<212> TYPE: PRT
<213> ORGANISM: Artificial
<220> FEATURE:
<223> OTHER INFORMATION: Synthetic Construct

<400> SEQUENCE: 50

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Phe Gly Glu Pro Val Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90
```

```
Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200

His Gln Gly Leu Ser Ser Pro Val Thr Lys Ser Phe Asn Arg Gly Glu
        205                 210                 215

Cys


<210> SEQ ID NO 51
<211> LENGTH: 726
<212> TYPE: DNA
<213> ORGANISM: Artificial
<220> FEATURE:
<223> OTHER INFORMATION: An artificially synthesized nucleotide sequence
<220> FEATURE:
<221> NAME/KEY: CDS
<222> LOCATION: (1)..(723)
<220> FEATURE:
<221> NAME/KEY: sig_peptide
<222> LOCATION: (1)..(66)
<220> FEATURE:
<221> NAME/KEY: mat_peptide
<222> LOCATION: (67)..(723)

<400> SEQUENCE: 51

atg aaa tac cta ttg cct acg gca gcc gct gga ttg tta tta ctc gcg       48
Met Lys Tyr Leu Leu Pro Thr Ala Ala Ala Gly Leu Leu Leu Leu Ala
        -20                 -15                 -10

gcc cag ccg gcc atg gcc gat gtt gtg atg act cag tct cca ctc tcc       96
Ala Gln Pro Ala Met Ala Asp Val Val Met Thr Gln Ser Pro Leu Ser
    -5              -1  1               5                   10

ctg ccc gtc acc ttt gga gag caa gtc tcc atc tcc tgc agg tct agt      144
Leu Pro Val Thr Phe Gly Glu Gln Val Ser Ile Ser Cys Arg Ser Ser
                15                  20                  25

cag agt ctt gca aac agt tat ggg aac acc tat ttg tct tgg tac ctg      192
Gln Ser Leu Ala Asn Ser Tyr Gly Asn Thr Tyr Leu Ser Trp Tyr Leu
            30                  35                  40

cag aag cca ggg cag tct cca cag ctc ctg atc tat ggg att tcc aac      240
Gln Lys Pro Gly Gln Ser Pro Gln Leu Leu Ile Tyr Gly Ile Ser Asn
        45                  50                  55

aga ttt tct ggg gtc cct gac agg ttc agt ggc agt gga tca ggc aca      288
Arg Phe Ser Gly Val Pro Asp Arg Phe Ser Gly Ser Gly Ser Gly Thr
    60                  65                  70

gat ttt aca ctg aaa atc agc aga gtg gag gct gag gat gtt ggg gtt      336
Asp Phe Thr Leu Lys Ile Ser Arg Val Glu Ala Glu Asp Val Gly Val
75                  80                  85                  90

tat tac tgc tta caa ggt aca cat cag ccg tac acg ttt ggc cag ggg      384
Tyr Tyr Cys Leu Gln Gly Thr His Gln Pro Tyr Thr Phe Gly Gln Gly
                95                  100                 105

acc aag ctg gag atc aaa cgt acg gtg gct gca cca tct gtc ttc atc      432
Thr Lys Leu Glu Ile Lys Arg Thr Val Ala Ala Pro Ser Val Phe Ile
            110                 115                 120
```

```
ttc ccg cca tct gat gag cag ttg aaa tct gga act gcc tct gtt gtg      480
Phe Pro Pro Ser Asp Glu Gln Leu Lys Ser Gly Thr Ala Ser Val Val
        125                 130                 135

tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
    140                 145                 150

gtg gat aac gcc ctc caa tcg ggt aac tcc cag gag agt gtc aca gag      576
Val Asp Asn Ala Leu Gln Ser Gly Asn Ser Gln Glu Ser Val Thr Glu
155                 160                 165                 170

cag gac agc aag gac agc acc tac agc ctc agc agc acc ctg acg ctg      624
Gln Asp Ser Lys Asp Ser Thr Tyr Ser Leu Ser Ser Thr Leu Thr Leu
                175                 180                 185

agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
            190                 195                 200

cat cag ggc ctg agc tcg ccc gtc aca aag agc ttc aac agg gga gag      720
His Gln Gly Leu Ser Ser Pro Val Thr Lys Ser Phe Asn Arg Gly Glu
        205                 210                 215

tgt tga                                                              726
Cys


<210> SEQ ID NO 52
<211> LENGTH: 241
<212> TYPE: PRT
<213> ORGANISM: Artificial
<220> FEATURE:
<223> OTHER INFORMATION: Synthetic Construct

<400> SEQUENCE: 52

Met Lys Tyr Leu Leu Pro Thr Ala Ala Ala Gly Leu Leu Leu Leu Ala
        -20                 -15                 -10

Ala Gln Pro Ala Met Ala Asp Val Val Met Thr Gln Ser Pro Leu Ser
    -5              -1  1               5                   10

Leu Pro Val Thr Phe Gly Glu Gln Val Ser Ile Ser Cys Arg Ser Ser
                15                  20                  25

Gln Ser Leu Ala Asn Ser Tyr Gly Asn Thr Tyr Leu Ser Trp Tyr Leu
            30                  35                  40

Gln Lys Pro Gly Gln Ser Pro Gln Leu Leu Ile Tyr Gly Ile Ser Asn
        45                  50                  55

Arg Phe Ser Gly Val Pro Asp Arg Phe Ser Gly Ser Gly Ser Gly Thr
    60                  65                  70

Asp Phe Thr Leu Lys Ile Ser Arg Val Glu Ala Glu Asp Val Gly Val
75                  80                  85                  90

Tyr Tyr Cys Leu Gln Gly Thr His Gln Pro Tyr Thr Phe Gly Gln Gly
                95                  100                 105

Thr Lys Leu Glu Ile Lys Arg Thr Val Ala Ala Pro Ser Val Phe Ile
            110                 115                 120

Phe Pro Pro Ser Asp Glu Gln Leu Lys Ser Gly Thr Ala Ser Val Val
        125                 130                 135

Cys Leu Leu Asn Asn Phe Tyr Pro Arg Glu Ala Lys Val Gln Trp Lys
    140                 145                 150

Val Asp Asn Ala Leu Gln Ser Gly Asn Ser Gln Glu Ser Val Thr Glu
155                 160                 165                 170

Gln Asp Ser Lys Asp Ser Thr Tyr Ser Leu Ser Ser Thr Leu Thr Leu
                175                 180                 185

Ser Lys Ala Asp Tyr Glu Lys His Lys Val Tyr Ala Cys Glu Val Thr
            190                 195                 200
```

```
His Gln Gly Leu Ser Ser Pro Val Thr Lys Ser Phe Asn Arg Gly Glu
        205                 210                 215

Cys


<210> SEQ ID NO 53
<211> LENGTH: 125
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Leu Gly Gly Tyr Cys Ser Gly Gly Ser Cys Pro Asn Asn Trp Phe
            100                 105                 110

Asp Pro Trp Gly Gln Gly Thr Leu Val Thr Val Ser Ser
        115                 120                 125


<210> SEQ ID NO 54
<211> LENGTH: 113
<212> TYPE: PRT
<213> ORGANISM: Homo sapiens

<400> SEQUENCE: 54

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg


<210> SEQ ID NO 55
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 55

gcgaattcac catggactgg acctggagca tccttttctt ggtggcagca gcaacaggtg     60
```

cccactccca ggttcagctg 80

<210> SEQ ID NO 56
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 56
gaagaagcct ggggcctcag tgaaggtctc ctgcaaggct tctggttaca cctttaccga 60
ctttgaaatg cactgggtgc 80

<210> SEQ ID NO 57
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 57
cttgagtgga tgggagatat tgatcctgga actggtgata ctgcctacaa tctgaagttc 60
aagggcagag tcaccatgac 80

<210> SEQ ID NO 58
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 58
cagcctacat ggagctgagg agcctgagat ctgacgacac ggccgtgtat tactgtgcgt 60
tgggggcctt tgtttactgg 80

<210> SEQ ID NO 59
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 59
gagaccttca ctgaggcccc aggcttcttc acctcagctc cagactgcac cagctgaacc 60
tgggagtggg cacctgttgc 80

<210> SEQ ID NO 60
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 60
tccaggatca atatctccca tccactcaag cccttgtcca ggggcctgtc gcacccagtg 60
catttcaaag tcggtaaagg 80

<210> SEQ ID NO 61
<211> LENGTH: 80
<212> TYPE: DNA
<213> ORGANISM: Artificial
<220> FEATURE:
<223> OTHER INFORMATION: An artificially synthesized primer sequence -continued

<400> SEQUENCE: 61
atctcaggct cctcagctcc atgtaggctg tgctcgtgga tgtgtctgtg gtcatggtga 60
ctctgccctt gaacttcaga 80

<210> SEQ ID NO 62
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 62
gcgctagctg aggagacggt gaccagggtt ccctggcccc aggggtcgaa ccagtaaaca 60
aaggccccca acgcacagta 80

<210> SEQ ID NO 63
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 63
gctgtcgacc accatgaaat acctattgcc tacggcagcc gctggattgt tattactcgc 60
ggcccagccg gccatggccg 80

<210> SEQ ID NO 64
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 64
ccactctccc tgcccgtcac ccctggagag ccggcctcca tctcctgcag gtctagtcag 60
agtcttgcaa acagttatgg 80

<210> SEQ ID NO 65
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 65
acctgcagaa gccagggcag tctccacagc tcctgatcta tgggatttcc aacagatttt 60
ctggggtccc tgacaggttc 80

<210> SEQ ID NO 66
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 66
agattttaca ctgaaaatca gcagagtgga ggctgaggat gttggggttt attactgctt 60
acaaggtaca catcagccgt 80

<210> SEQ ID NO 67
<211> LENGTH: 80
<212> TYPE: DNA

<213> ORGANISM: Artificial
<220> FEATURE:
<223> OTHER INFORMATION: An artificially synthesized primer sequence

<400> SEQUENCE: 67
ctctccaggg gtgacgggca gggagagtgg agactgagtc atcacaacat cggccatggc 60
cggctgggcc gcgagtaata 80

<210> SEQ ID NO 68
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 68
gctgtggaga ctgccctggc ttctgcaggt accaagacaa ataggtgttc ccataactgt 60
ttgcaagact ctgactagac 80

<210> SEQ ID NO 69
<211> LENGTH: 80
<212> TYPE: DNA
<213> ORGANISM: Artificial
<220> FEATURE:
<223> OTHER INFORMATION: An artificially synthesized primer sequence

<400> SEQUENCE: 69
tccactctgc tgattttcag tgtaaaatct gtgcctgatc cactgccact gaacctgtca 60
gggaccccag aaaatctgtt 80

<210> SEQ ID NO 70
<211> LENGTH: 74
<212> TYPE: DNA
<213> ORGANISM: Artificial
<220> FEATURE:
<223> OTHER INFORMATION: An artificially synthesized primer sequence

<400> SEQUENCE: 70
cggcgtacgt ttgatctcca gcttggtccc ctggccaaac gtgtacggct gatgtgtacc 60
ttgtaagcag taat 74

<210> SEQ ID NO 71
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 71
gcgaattcac catggactgg acctggagca 30

<210> SEQ ID NO 72
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 72
cgcgctagct gaggagacgg tgaccagggt 30

<210> SEQ ID NO 73
<211> LENGTH: 30
<212> TYPE: DNA

<213> ORGANISM: Artificial
<220> FEATURE:
<223> OTHER INFORMATION: An artificially synthesized primer sequence

<400> SEQUENCE: 73
gctgtcgacc accatgaaat acctattgcc 30

<210> SEQ ID NO 74
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 74
cggcgtacgt ttgatctcca gcttggtccc 30

<210> SEQ ID NO 75
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 75
ggggcctttg tttactgggg ccagggaacc 30

<210> SEQ ID NO 76
<211> LENGTH: 29
<212> TYPE: DNA
<213> ORGANISM: Artificial
<220> FEATURE:
<223> OTHER INFORMATION: An artificially synthesized primer sequence

<400> SEQUENCE: 76
ggttccctgg ccccagtaaa caaggcccc 29

<210> SEQ ID NO 77
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 77
taacaccgcc ccggttttcc 20

<210> SEQ ID NO 78
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 78
agtagagtcc tgaggactgt agg 23

<210> SEQ ID NO 79
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 79
tctaggtgct gtccttgctg tcc 23

<210> SEQ ID NO 80
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 80
tagtcagagt cttgcaaaca gttatgggaa 30

<210> SEQ ID NO 81
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 81
caaataggtg ttcccataac tgtttgcaag 30

<210> SEQ ID NO 82
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 82
atggccgatg ttgtggtgac tcagtctcca 30

<210> SEQ ID NO 83
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 83
tggagactga gtcaccacaa catcggccat 30

<210> SEQ ID NO 84
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 84
ctgcccgtca cctttggaga gccggcctcc 30

<210> SEQ ID NO 85
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 85
ggaggccggc tctccaaagg tgacgggcag 30

<210> SEQ ID NO 86
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 86
cacccctgga gagcaagcct ccatctcctg 30

<210> SEQ ID NO 87
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 87
caggagatgg aggcttgctc tccaggggtg 30

<210> SEQ ID NO 88
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 88
ccgtcacctt tggagagcaa gcctccatct 30

<210> SEQ ID NO 89
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 89
agatggaggc ttgctctcca aaggtgacgg 30

<210> SEQ ID NO 90
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 90
tggagagccg gtctccatct cctgcaggtc 30

<210> SEQ ID NO 91
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 91
gacctgcagg agatggagac cggctctcca 30

<210> SEQ ID NO 92
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 92
tggagagcaa gtctccatct cctgcaggtc 30

<210> SEQ ID NO 93
<211> LENGTH: 30
<212> TYPE: DNA

-continued

```
<213> ORGANISM: Artificial
<220> FEATURE:
<223> OTHER INFORMATION: An artificially synthesized primer sequence

<400> SEQUENCE: 93

gacctgcagg agatggagac ttgctctcca                                    30
```